(12) United States Patent
Kurokawa et al.

(10) Patent No.: US 8,345,249 B2
(45) Date of Patent: Jan. 1, 2013

(54) LIQUID SAMPLE ANALYZING METHOD

(75) Inventors: Hideyuki Kurokawa, Ehime (JP); Koji Miyoshi, Ehime (JP); Masahiro Aga, Ehime (JP); Kenji Murakami, Ehime (JP); Takahiko Tanida, Ehime (JP); Ryosuke Yamada, Ehime (JP)

(73) Assignee: Panasonic Corporation, Osaka (JP)

( * ) Notice: Subject to any disclaimer, the term of this patent is extended or adjusted under 35 U.S.C. 154(b) by 312 days.

(21) Appl. No.: 12/935,156

(22) PCT Filed: Mar. 26, 2009

(86) PCT No.: PCT/JP2009/001347
§ 371 (c)(1),
(2), (4) Date: Sep. 28, 2010

(87) PCT Pub. No.: WO2009/128205
PCT Pub. Date: Oct. 22, 2009

(65) Prior Publication Data
US 2011/0032525 A1    Feb. 10, 2011

(30) Foreign Application Priority Data

Apr. 18, 2008 (JP) ................................. 2008-108401
Aug. 29, 2008 (JP) ................................. 2008-220599
Oct. 29, 2008 (JP) ................................. 2008-277525

(51) Int. Cl.
*G01N 33/48* (2006.01)
*G01N 21/00* (2006.01)
(52) U.S. Cl. ........................... 356/436; 356/433; 356/39

(58) Field of Classification Search .......... 356/433–436, 356/39, 402; 422/82.05, 68.1; 436/514
See application file for complete search history.

(56) References Cited

U.S. PATENT DOCUMENTS

| 5,184,359 | A | | 2/1993 | Tsukamura et al. |
| 5,231,576 | A | * | 7/1993 | Suzuki et al. .................... 356/39 |
| 5,281,395 | A | * | 1/1994 | Markart et al. ............ 422/82.05 |
| 6,707,554 | B1 | | 3/2004 | Miltner et al. |
| 6,847,451 | B2 | * | 1/2005 | Pugh ............................. 356/436 |
| 6,908,593 | B1 | * | 6/2005 | Shartle ......................... 422/417 |

FOREIGN PATENT DOCUMENTS

| JP | 04-160362 | 6/1992 |
| JP | 07-005110 | 1/1995 |
| JP | 09-318544 | 12/1997 |
| JP | 2000-266752 | 9/2000 |
| JP | 2001-004613 | 1/2001 |

(Continued)

*Primary Examiner* — Layla Lauchman
(74) *Attorney, Agent, or Firm* — Hamre, Schumann, Mueller & Larson, P.C.

(57) ABSTRACT

Provided is a liquid sample analyzing method for analyzing an analyte in a liquid sample by using a test piece (1) on which overflow blocking lines (7) are formed to prevent the liquid sample from flowing to the outside from a passage region (3a) of an extended layer (3). In a state in which the liquid sample is not extended in the passage region (3a) of the extended region (3), the test piece (1) is measured so as to cross the passage region (3a) of the extended layer (3) and the overflow blocking lines (7). Thus in a state in which a difference in brightness is large between the passage region (3a) of the extended region (3) and the overflow blocking lines (7), it is possible to properly recognize the boundary portions between the passage region (3a) of the extended region (3) and the overflow blocking lines (7).

16 Claims, 19 Drawing Sheets

FOREIGN PATENT DOCUMENTS

| | | |
|---|---|---|
| JP | 2002-257837 | 9/2002 |
| JP | 3542999 | 4/2004 |
| JP | 2005-030984 | 2/2005 |
| JP | 2005-338101 | 12/2005 |
| WO | 01/92884 | 12/2001 |

* cited by examiner

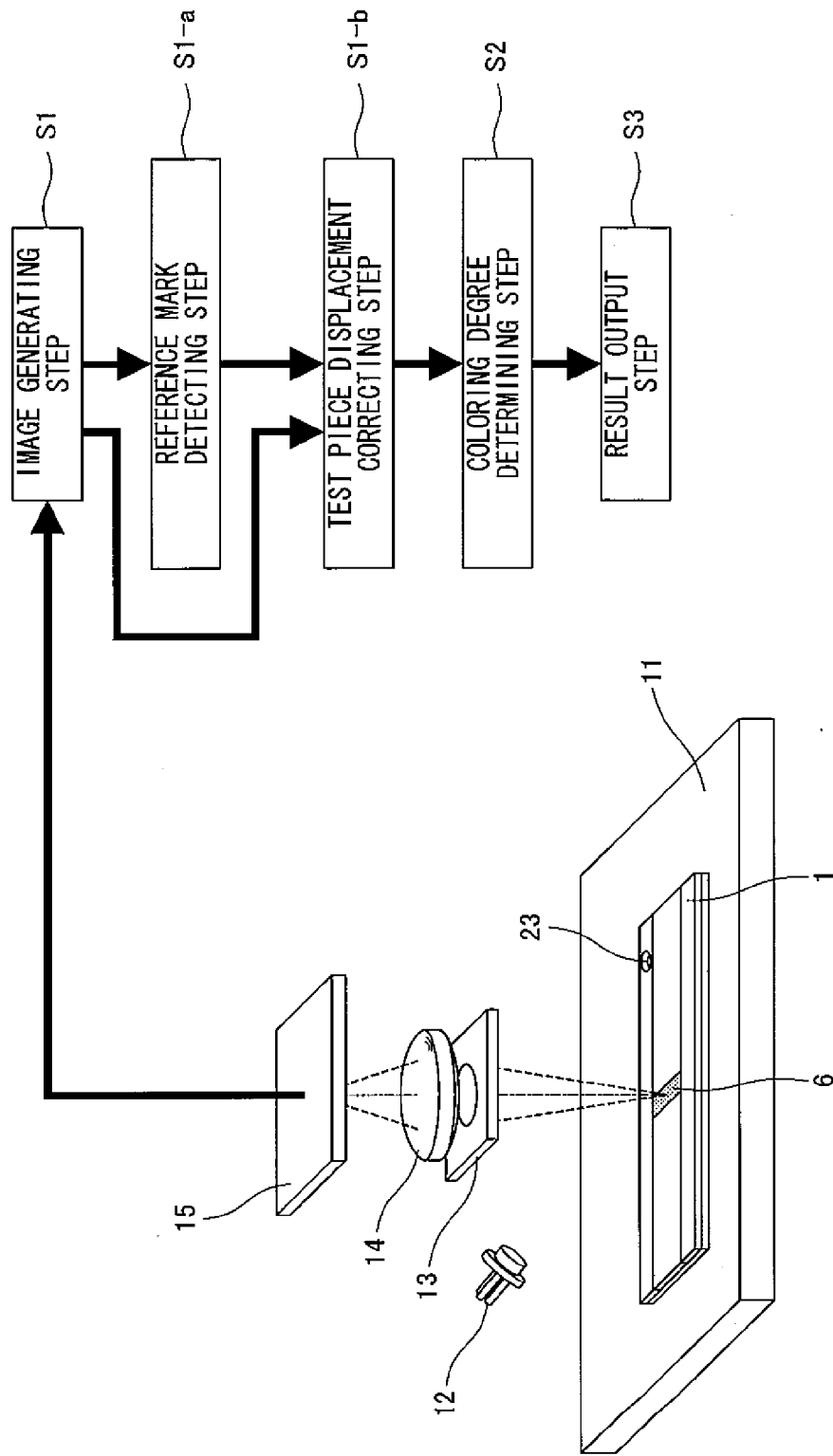

FIG. 24
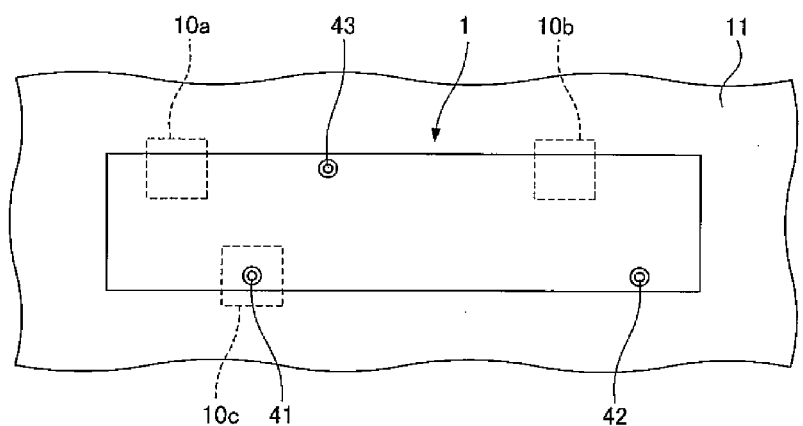
FIG. 25
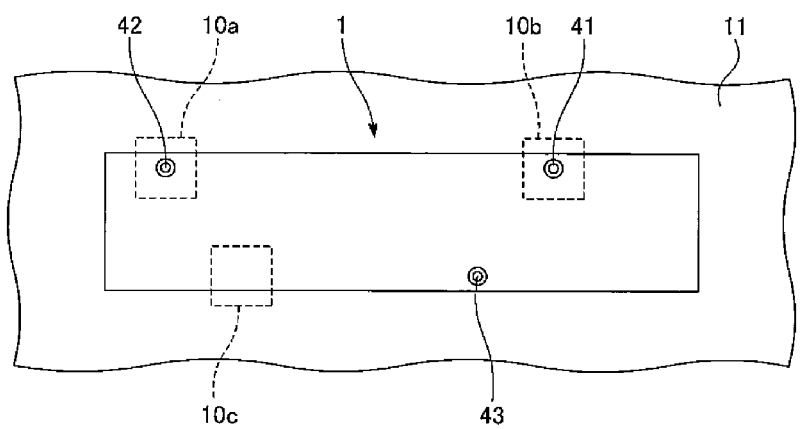
FIG. 26
|         | 10a | 10b | 10c |
|---------|-----|-----|-----|
| FIG. 22 | Y   | Y   | Y   |
| FIG. 23 | N   | N   | N   |
| FIG. 24 | N   | N   | Y   |
| FIG. 25 | Y   | Y   | N   |
(Y: REFERENCE MARK CONTAINED, N: NO REFERENCE MARKS CONTAINED)

LIQUID SAMPLE ANALYZING METHOD

TECHNICAL FIELD

The present invention relates to a liquid sample analyzing method in which a target analyte contained in a liquid sample is analyzed using an optical signal detecting method.

BACKGROUND ART

As a technique of measuring and analyzing a target analyte contained in a liquid sample such as blood, plasma, and urine, a liquid sample analyzing method and a liquid sample analyzing apparatus have been known in which a liquid sample is added to a test piece called a biosensor, the liquid sample is extended on an extended layer on the test piece by using chromatography, a target analyte immobilized at a predetermined point is read using the optical property of the target analyte, and the target analyte in the liquid sample is analyzed (for example, patent documents 1 and 2).

As shown in FIG. 5(a), a test piece 20 is configured such that an extended layer 3 containing a porous carrier is provided on a support 2 shaped like a rectangular thin plate, an added portion (so-called dropped portion) 4 for receiving a liquid sample is provided on one end of the test piece 20, and the liquid sample added to the added portion 4 is extended over the extended layer 3 by capillarity. On the extended layer 3, a labeled reagent portion 5 containing a labeled reagent is provided near the added portion and an immobilized reagent portion 6 containing an immobilized specific antibody is provided at a predetermined point. When a liquid sample such as blood and plasma is added to the added portion 4, the liquid sample is extended over the extended layer 3 on the test piece 20 while reacting with the labeled reagent of the labeled reagent portion 5, the labeled reagent having being bound by a specific antibody (different from the specific antibody of the immobilized reagent portion 6). Further, the liquid sample undergoes a combination reaction with the specific antibody of the immobilized reagent portion 6, so that the immobilized reagent portion 6 is colored according to the concentration of a target analyte in the liquid sample. After that, the liquid sample analyzing apparatus measures the coloring of the immobilized reagent portion 6 of a test piece 1, converts the coloring into the concentration of the target analyte, and outputs the analysis result.

As shown in FIG. 6, a liquid sample analyzing apparatus 10' includes: a holder 11 that holds the test piece 20 placed on the holder 11; a light source 12 that emits light to the test piece 20 and is made up of, e.g., a lamp, a light-emitting diode, or a semiconductor laser; a diaphragm 13 that limits scattered light (transmitted light or reflected light) from the light source 12; a condenser lens 14 that focuses light having passed through the diaphragm 13; an image element 15 such as a CCD on which the light is focused to form an image of the surface of the test piece 20; and a control unit (not shown) that converts an electric signal from the image element 15 into a digital signal, performs processing such as image processing to calculate as an absorbance the degree of coloring (brightness) of the immobilized reagent portion 6 serving as a colored portion on the test piece 20, calculates the concentration of a target analyte in a liquid sample by using the absorbance according to a stored concentration conversion formula, and outputs the concentration. Advantageously, since the image element 15 such as a CCD is used, it is possible to remove a colored portion in the background of the extended layer 3 of the test piece 20 by a subtraction and increase the accuracy of measurement by correcting the coloring through color tone correction.

FIG. 20 shows a measurement method using a test piece according to the prior art.

Reference numeral 1 denotes the test piece containing the immobilized reagent portion 6 that is colored according to the concentration of a measurement object in a liquid sample. An optical system for reading the degree of coloring of the immobilized reagent portion 6 is made up of the light source 12, the diaphragm 13, the condenser lens 14, and the image element 15.

The test piece 1 is irradiated with light from the light source 12, and the light scattered on the surface of the test piece 1 is received by the image element 15 through the diaphragm 13 and the condenser lens 14.

The step of processing an image captured by the image element 15 includes image generating step S1, coloring degree determining step S2, and result output step S3.

In the image generating step S1, an image signal outputted from the image element 15 is stored as a gray image in an image memory (not shown). In the coloring degree determining step S2, the degree of coloring of the immobilized reagent portion 6 is calculated. In the result output step S3, the measurement result is outputted to a display device (not shown) such as a liquid crystal display.

On this test piece 20, when both sides of the extended layer 3 of the test piece 20 are opened, the liquid sample and the labeled regent that are extended over the extended layer 3 by capillarity may flow or evaporate out of both sides of the extended layer 3. Thus a large quantity of liquid sample may be necessary or the penetration direction may vary and cause unstable coloring. In order to address this problem, patent document 3 proposes a configuration in which both sides of a test piece are sealed by melting and hardening with laser light, the sides being parallel to the extending direction (penetration direction) of the test piece.

With this configuration, both sides of the test piece are sealed to prevent a liquid sample and a labeled reagent from evaporating or flowing out of both sides of the test piece. Thus it is possible to reduce the quantities of the liquid sample and the labeled reagent and improve the accuracy by flow adjustment such that the liquid sample and the labeled reagent are properly extended. As shown in FIG. 5(b), the extended layer 3 may be partially melted and hardened by emitting laser light to a portion disposed inside both sides of a test piece 20' in the width direction of the test piece 20', that is, by emitting laser light along lines extended in the longitudinal direction of the test piece 20' along both sides of the test piece 20', so that a passage region 3a where the liquid sample flows on the extended layer 3 is smaller in width than the test piece 20'. In FIG. 5(b), reference numeral 7 denotes overflow blocking lines for preventing the liquid sample and the labeled reagent from extending and flowing out of both sides of the test piece 20' (in the width direction of the test piece 20'). The overflow blocking lines 7 are formed by melting and hardening with laser light. Reference character 3a denotes the passage region of the extended layer 3. The liquid sample and the labeled reagent actually pass through the passage region. Reference character 3b denotes non-passage regions where the liquid sample and the labeled reagent do not flow on the extended layer 3. In FIG. 5(b), the two overflow blocking lines 7 are formed at each of two points arranged in the width direction of the extended layer 3.

In this configuration, the overflow blocking lines 7 substantially parallel to both sides of the test piece 20' are formed inside both sides of the test piece 20', thereby substantially reducing the passage width of the extended layer 3 on which the liquid sample and the labeled reagent are extended. This configuration can reduce the required quantity of the liquid sample. Further, the immobilized reagent portion 6 serving as a colored portion and the labeled reagent portion 5 are reduced in width according to the passage width. Thus it is possible to reduce the quantities of the immobilized reagent and the labeled reagent.

As has been discussed, the overflow blocking lines 7 are formed on the test piece 20' such that the passage width of the extended layer 3 on which the liquid sample and the labeled reagent are extended is substantially smaller than the width of the test piece 20'. In this case, coloring occurs only at points disposed inside the overflow blocking lines 7 (passage region 3a) in the width direction of the test piece. Thus in the case of the test piece 20' on which the overflow blocking lines 7 are formed thus, when the degree of coloring is measured on the immobilized reagent portion 6 serving as a colored portion, it is preferable that the width of the passage region 3a substantially acting as the extended layer 3 is recognized beforehand and a portion where the immobilized reagent portion 6 is provided is set as a measured region.

However, actually because of various factors reducing positioning accuracy, e.g., a displacement of the test piece 20' fixed on the holder 11 and displacements of the immobilized reagent portion 6, the extended layer 3, and the overflow blocking lines 7 on the test piece 20' in a manufacturing process, it cannot be assumed that the passage region 3a and the immobilized reagent portion 6 are correctly placed at the same positions in each measurement. Therefore, in each measurement, it is preferable to recognize the test piece 20' through the image element 15 and detect the passage width of the extended layer 3.

In a conventional method of recognizing the passage width of the extended layer 3, an image of the extended layer 3 is generated in a state in which the liquid sample is added to the test piece 20' and is extended over the extended layer 3. Further, a pixel is detected on a scanning line L1 crossing the extended layer 3 containing the overflow blocking lines 7. FIG. 7 shows that the test piece 20' (see FIG. 5(b)) on which the overflow blocking lines 7 are formed is measured by the liquid sample analyzing apparatus 10'. FIG. 8(a) shows an example of an image. FIG. 8(b) shows brightness at a point corresponding to the image. It is determined that a region from the center of the extended layer 3 in the width direction to small fluctuations in brightness, for example, a region D of FIG. 8(b) is located inside the overflow blocking lines 7.
Patent document 1: Japanese Patent Laid-Open No. 7-5110
Patent document 2: Japanese Patent Laid-Open No. 2001-4613
Patent document 3: Japanese Patent No. 3542999
Patent document 4: Japanese Patent Laid-Open No. 2000-266752
Patent document 5: International Publication No. WO 01/092884

DISCLOSURE OF THE INVENTION

Problems to be Solved by the Invention

However, even when the extended layer 3 is measured in the width direction with the extended liquid sample in order to recognize the passage width of the extended layer 3 of the test piece 20', it is not possible to properly recognize the boundary portions of the overflow blocking lines 7. Thus disadvantageously, the accuracy of setting may decrease in a measurement range and measurement data may become less reliable.

To be specific, as shown in FIGS. 8(a) and 8(b), the liquid sample extended over the extended layer 3 penetrates the passage region 3a of the extended layer 3 containing a porous carrier, and then the liquid sample spreads to the overflow blocking lines 7. Thus a difference in brightness between the passage region 3a of the extended layer 3 and the overflow blocking lines 7 decreases and the boundary portions of the overflow blocking lines 7 become blurred, so that the overflow blocking lines 7 may be erroneously recognized as a part of the passage region 3a of the extended layer 3. When the overflow blocking lines 7 are erroneously recognized, the measured passage width of the extended layer 3 and the measured width of the immobilized reagent portion 6 as inputted data may be erroneously recognized as larger widths, so that the reliability of measurement data may decrease.

Further, depending upon the liquid sample, coloring in the background of the passage region 3a of the extended layer 3 varies among the test pieces 20', so that brightness and the degree of coloring in each measurement also fluctuate accordingly. Consequently, it is difficult to properly set the threshold value of fluctuations in brightness. The threshold value is a criterion for recognizing the passage width of the extended layer 3. Moreover, it is difficult to make a distinction to recognize the passage width of the extended layer 3, so that the reliability may decrease and the distinction may require a long period of time.

When the liquid sample is extended over the extended layer 3, the degree of coloring may vary (not shown) in the passage region 3a of the extended layer 3 in the width direction. In this case, the passage width of the extended layer 3 may not be properly read.

The present invention has been devised to solve the problems. An object of the present invention is to provide a liquid sample analyzing method by which boundaries between the passage region of an extended layer and overflow blocking lines can be properly recognized on a test piece including the overflow blocking lines for preventing a liquid sample from flowing to the outside from the passage region of the extended layer.

Means for Solving the Problems

In order to solve the problems, a liquid sample analyzing method according to the present invention uses a test piece, the test piece including an extended layer on which a liquid sample is extended, the extended layer including: overflow blocking lines for preventing the liquid sample from flowing to the outside from the passage region of the extended layer; and a colored portion that is provided on a part of the passage region of the extended layer and contains an immobilized reagent, the analyzing method including: extending the liquid sample added to the test piece, in the passage region of the extended layer; and analyzing a target analyte in the liquid sample by optically detecting the coloring of the colored portion, wherein in a state in which the liquid sample is not extended in the passage region of the extended layer, the analyzing method further includes: optically measuring the test piece so as to cross the passage region of the extended layer and the overflow blocking lines; and deciding the passage width of the extended layer based on the measurement data.

According to the liquid sample analyzing method, the test piece is measured so as to cross the passage region of the extended layer and the overflow blocking lines in a state in which the liquid sample is not extended in the passage region of the extended layer. Thus it is possible to properly recognize boundary portions between the passage region of the extended layer and the overflow blocking lines in a state in which the liquid sample is not extended in the passage region of the extended layer and a difference in brightness is large between the passage region of the extended layer and the overflow blocking lines. Further, in a state in which the liquid sample is not extended, the passage of the extended layer and the overflow blocking lines are colored substantially as in product shipment. It is therefore possible to easily and properly set a brightness fluctuation threshold value that is a criterion for distinguishing between the passage region of the extended layer and the overflow blocking lines. Moreover, the passage region of the extended layer is substantially uniformly colored. Consequently, it is possible to correctly and quickly recognize the boundary portions between the passage region of the extended layer and the overflow blocking lines, and properly recognize the width of the passage region of the extended layer that is substantially uniformly colored.

According to the present invention, the passage width of the extended layer is decided by capturing an image containing the test piece on an image element and scanning the pixels of the image so as to cross the passage region of the extended layer and the overflow blocking lines.

The test piece is measured so as to cross the passage region of the extended layer and the overflow blocking lines, based on the image captured when the liquid sample is not extended in the passage region of the extended layer. Thus it is possible to properly recognize the boundary portions between the passage region of the extended layer and the overflow blocking lines in a state in which the liquid sample is not extended in the passage region of the extended layer and a difference in brightness is large between the passage region of the extended layer and the overflow blocking lines.

According to the present invention, the colored portion is measured or measurement information about the colored portion is inputted based on decision information about the passage width of the extended layer.

According to this method, it is possible to measure the colored portion or input the measurement information of the colored portion in a state in which the passage width of the extended layer is properly and correctly detected, thereby improving the accuracy and reliability of analysis.

According to the present invention, the overflow blocking lines are formed by melting and hardening a part of the extended layer containing a porous carrier, with laser light emitted to the extended layer.

According to the present invention, the liquid sample added to the test piece is extended and measured by chromatography.

The test piece includes at least one reference mark formed at a position relative to the colored portion, the at least one reference mark including a hole penetrating the extended layer from a surface containing the colored portion.

The test piece includes: a support covering the opposite surface of the extended layer from the colored portion contained in the other surface of the extended layer; and at least one reference mark that is a hole penetrating the extended layer and the support from the surface containing the colored portion.

The test piece includes: a support that covers the opposite surface of the extended layer from the colored portion contained in the other surface of the extended layer and partially contains an exposed portion near the extended layer; and a reference mark that is a hole penetrating the support from the exposed portion.

The test piece includes: a light shielding layer that is bonded to the extended layer directly or via a support and is darker than the surface color of the extended layer; and a reference mark that is a hole penetrating the extended layer from a surface containing the colored portion, the hole partially exposing the light shielding layer.

The reference mark is a hole that is formed by laser melting and is circular in cross section along the surface containing the colored portion.

The at least one reference mark includes multiple reference marks formed at asymmetric positions with respect to a center line parallel to the extension direction of the extended layer and a central point.

The at least one reference mark is a printed mark formed instead of the through hole, at a point corresponding to the opening of the through hole.

The liquid sample analyzing method includes: an image generating step of generating a gray image by imaging, with an image sensor, the surface containing the colored portion on the test piece before the optical measurement; a reference mark detecting step of calculating, from the gray image, a displacement pre-correction reference mark position indicating the position of the reference mark of the test piece; and a sensor displacement correcting step of performing linear coordinate transformation on the gray image such that the displacement pre-correction reference mark position is aligned with a corresponding displacement post-correction reference mark position.

The liquid sample analyzing method includes: an image generating step of generating a gray image by imaging, with an image sensor, the surface containing the colored portion on the test piece before the optical measurement; a reference mark detecting step of calculating, from the gray image, displacement pre-correction reference mark positions indicating the positions of the reference marks of the test piece; an incorrect mounting detecting step of confirming whether the displacement pre-correction reference mark positions are respectively contained in predetermined reference mark searching ranges; a processing stopping step of stopping processing when the displacement pre-correction reference mark positions are all disposed outside the predetermined reference mark searching ranges in the incorrect mounting detecting step; and a sensor displacement correcting step of performing linear coordinate transformation on the gray image such that the displacement pre-correction reference mark positions are aligned with respective displacement post-correction reference mark positions when the displacement pre-correction reference mark positions are contained in the respective predetermined reference mark searching ranges in the incorrect mounting detecting step.

In the reference mark detecting step, the gray image is binarized by a predetermined threshold value and the displacement pre-correction reference mark position of the at least one reference mark is the barycenter of a connected component.

Advantage of the Invention

According to the present invention, in a state in which a liquid sample is not extended in the passage region of an extended layer, a test piece is measured so as to cross the passage region of the extended layer and overflow blocking lines. Thus it is possible to properly recognize boundary portions between the passage region of the extended layer and the overflow blocking lines in a state in which a difference in brightness is large between the passage region of the extended layer and the overflow blocking lines. It is therefore possible to properly set the passage width of the extended layer and the measurement range of a colored portion and measure the colored portion in the properly set measurement range, thereby improving the reliability and accuracy of measurement. Further, in a state in which the liquid sample is not extended, the passage region of the extended layer and the overflow blocking lines are colored substantially as in product shipment. It is therefore possible to properly and relatively easily set the brightness fluctuation threshold value that is a criterion for distinguishing between the passage region of the extended layer and the overflow blocking line and it is possible to correctly and quickly recognize the boundary portion between the passage region of the extended layer and the overflow blocking line. Further, substantially uniform coloring is obtained in the passage region of the extended layer in the width direction during measurement. Thus it is possible to properly recognize the width of the passage region of the extended layer and also improve the reliability and accuracy of measurement.

BRIEF DESCRIPTION OF THE DRAWINGS

FIG. 9 is a structural diagram showing a measuring method using a test piece according to a second embodiment of the present invention;

FIG. 24 shows that the test piece is flipped and mounted according to the fifth embodiment;

FIG. 25 shows that the test piece is mounted after being flipped and turned around according to the fifth embodiment; and FIG. 26 shows the recognition patterns of the reference marks according to the fifth embodiment.

BEST MODE FOR CARRYING OUT THE INVENTION

Figure 1:
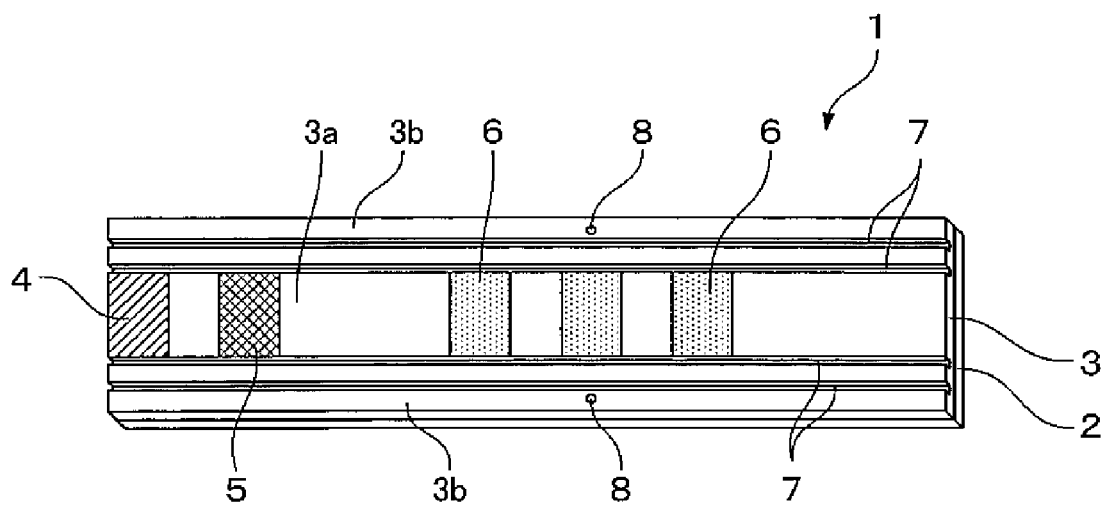
FIG. 1 is a perspective view showing a test piece used for a liquid sample analyzing method according to a first embodiment of the present invention.

A liquid sample analyzing method according to embodiments of the present invention will be described below in accordance with the accompanying drawings. Constituent elements having the same functions as those of the test pieces 20 and 20' and the liquid sample analyzing apparatus 10' of the prior art will be indicated by the same reference numerals.

First Embodiment

First, the following will describe a test piece used for a liquid sample analyzing method of the present invention. In the liquid sample analyzing method of the present invention, a test piece 1 shown in FIG. 1 is used. As shown in FIG. 1, the test piece 1 is configured such that an extended layer 3 is provided on a support 2 that is a thin rectangular plate made of a liquid impermeable material such as polyethylene terephthalate. The extended layer 3 contains a porous carrier such as nitrocellulose and glass filter paper and is a thin rectangular plate substantially shaped like the support 2. On the extended layer 3 of the test piece 1, overflow blocking lines 7 are formed at positions located inside both sides of the test piece 1 in the width direction. The overflow blocking lines 7 are formed by melting and hardening the porous carrier with laser light emitted substantially in parallel with both sides of the test piece 1. When a liquid sample such as blood and plasma is added, a region located inside the overflow blocking lines 7 of the extended layer 3 in the width direction acts as a passage region 3a that receives the liquid sample and a labeled reagent, which will be describe later. Further, regions outside the overflow blocking lines 7 act as non-passage regions 3b that do not receive the liquid sample and the labeled reagent, which will be describe later. In the present embodiment, in order to more reliably prevent the liquid sample and the labeled reagent from flowing into the non-passage regions 3b, the two overflow blocking lines 7 arranged in the width direction are formed on each side of the extended layer 3. The present invention is not limited to this configuration. A single overflow blocking line 7 may be formed on each side of the passage region 3a or three or more overflow blocking lines 7 may be formed on each side of the passage region 3a.

On one end of the test piece 1, an added portion (so-called dropped portion) 4 is provided on which the liquid sample is added (dropped). The liquid sample added to the added portion 4 flows through (penetrates) the passage region 3a of the extended layer 3 while being sucked by capillarity, so that the liquid sample is extended to the other end of the test piece 1. Further, in the passage region 3a of the extended layer 3, a labeled reagent portion 5 containing the labeled reagent is provided near the added portion 4 and immobilized reagent portions 6, each of which is a colored portion containing an immobilized specific antibody, are provided at predetermined points (between the labeled reagent portion 5 and the other end of the test piece 1). When the liquid sample such as blood and plasma is added to the added portion 4, the liquid sample is extended in the passage region 3a of the extended layer 3 on the test piece 1 while reacting with the labeled reagent bound by a specific antibody (different from the specific antibody of the immobilized reagent portions 6). Further, the liquid sample undergoes a combination reaction with the specific antibody of the immobilized reagent portion 6, so that the immobilized reagent portion 6 acts as a colored portion that is colored according to the concentration of a target analyte in the liquid sample. After that, a sample analyzing apparatus 10, which will be described later, measures the coloring of the immobilized reagent portion 6 of the test piece 1, converts the coloring into the concentration of the target analyte, and outputs the analysis result.

On the test piece 1 shown in FIG. 1 of the first embodiment, the immobilized reagent portions 6 serving as colored portions are provided at three points. The present invention is not limited to this configuration and the number of immobilized reagent portions 6 may be optionally determined. For example, the immobilized reagent portions 6 may be provided at one, two, or at least four points. Moreover, on the test piece 1 shown in FIG. 1 of the first embodiment, holes 8 for detecting the positions of the immobilized reagent portions 6 in the longitudinal direction of the test piece 1 are formed at points in the non-passage region 3b of the extended layer 3. The present invention is not limited to this configuration.

In this configuration, the overflow blocking lines 7 are formed inside both sides of the test piece 1 such that the overflow blocking lines 7 are substantially in parallel with both sides of the test piece 1, substantially reducing the passage width of the extended layer 3 in which the liquid sample and the labeled reagent are extended. Thus it is possible to reduce the required quantity of the liquid sample. Further, the immobilized reagent portions 6 serving as colored portions and the labeled reagent portion 5 are reduced in width according to the passage width. Thus it is possible to reduce the quantities of the immobilized reagent and the labeled reagent as compared with the case where the immobilized reagent portions 6 and the labeled reagent portion 5 are provided over the width of the extended layer 3.

Preferably, the surface of the extended layer 3 (at least the surface of the passage region 3a of the extended layer 3) is covered with a liquid impermeable sheet (not shown). More preferably, the liquid impermeable sheet covers a region from a portion of the added portion 4 or a portion near the added portion 4 to at least the immobilized reagent portion 6 and the liquid impermeable sheet does not cover the downstream end of the passage region 3a of the extended layer 3 (the other end of the test piece 1). Thus, it is possible to prevent the liquid sample from flowing to the outside from the passage region 3a of the extended layer 3 in the width direction and prevent evaporation and drying at a point covered with the liquid impermeable sheet on the surface of the passage region 3a of the extended layer 3, thereby minimizing the required quantity of the liquid sample. The downstream end of the passage region 3a of the extended layer 3 is not covered with the liquid impermeable sheet and thus at the downstream end not covered with the liquid impermeable sheet, an extended liquid (a liquid such as the liquid sample and the labeled reagent) evaporates and causes drying. Thus, the extension of the liquid sample from an upstream region to a downstream region is advantageously accelerated in an extension flow direction (chromatography flow direction).

The following will describe the liquid sample analyzing apparatus used for the liquid sample analyzing method according to the first embodiment of the present invention.

Figure 2:
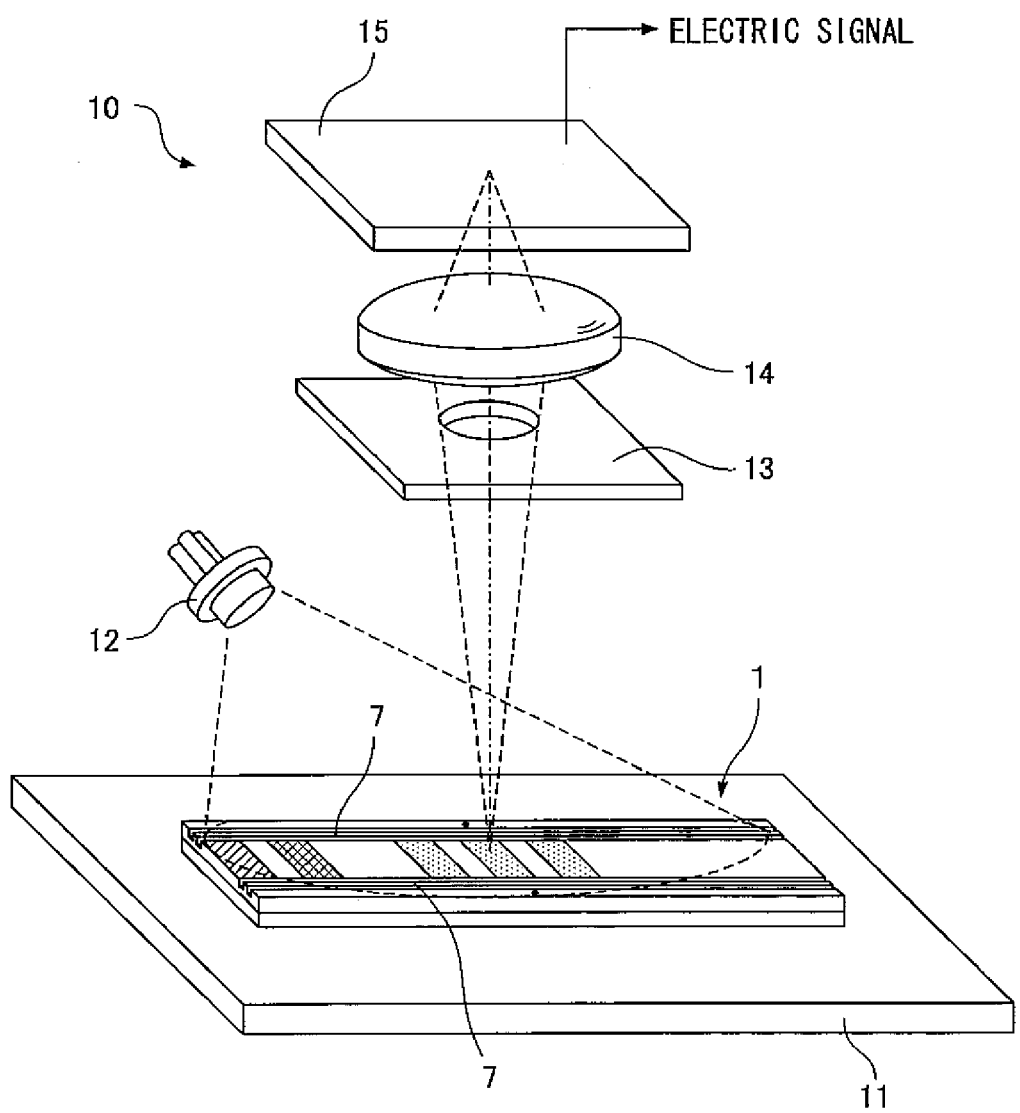
FIG. 2 is a perspective view schematically showing a liquid sample analyzing apparatus used for the liquid sample analyzing method according to the first embodiment of the present invention.
Figure 6:
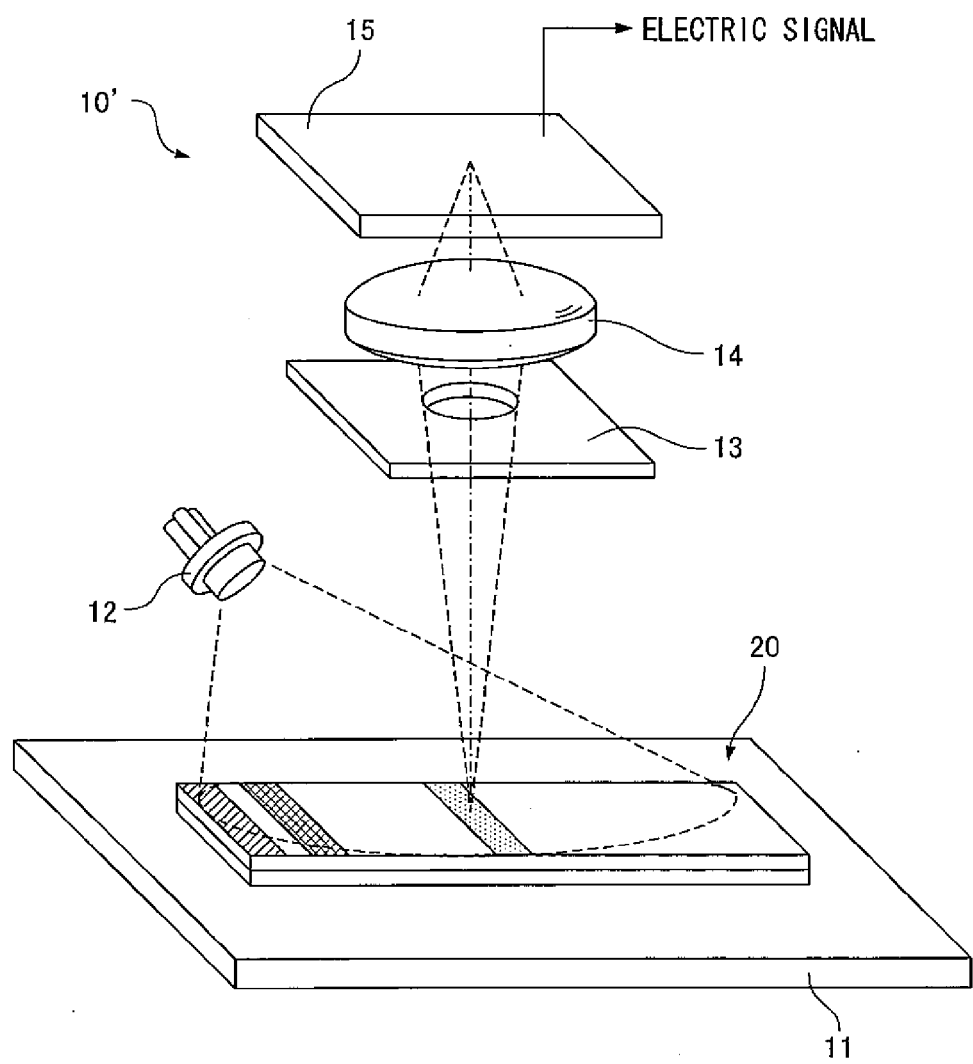
FIG. 6 is a perspective view schematically showing that the test piece having no overflow blocking lines is measured by a liquid sample analyzing apparatus according to the prior art.
Figure 7:
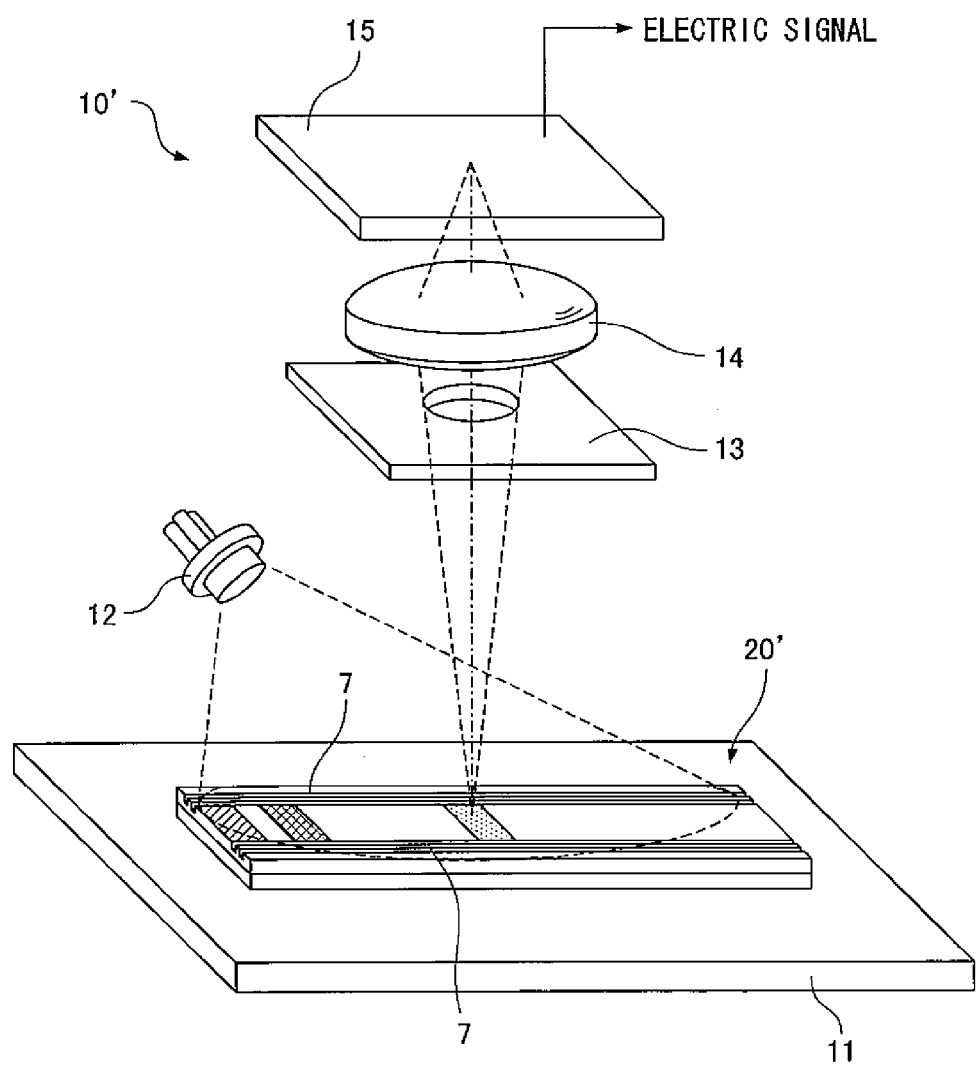
FIG. 7 is a perspective view schematically showing that the test piece having the overflow blocking lines is measured by the liquid sample analyzing apparatus according to the prior art.
Figure 8A:
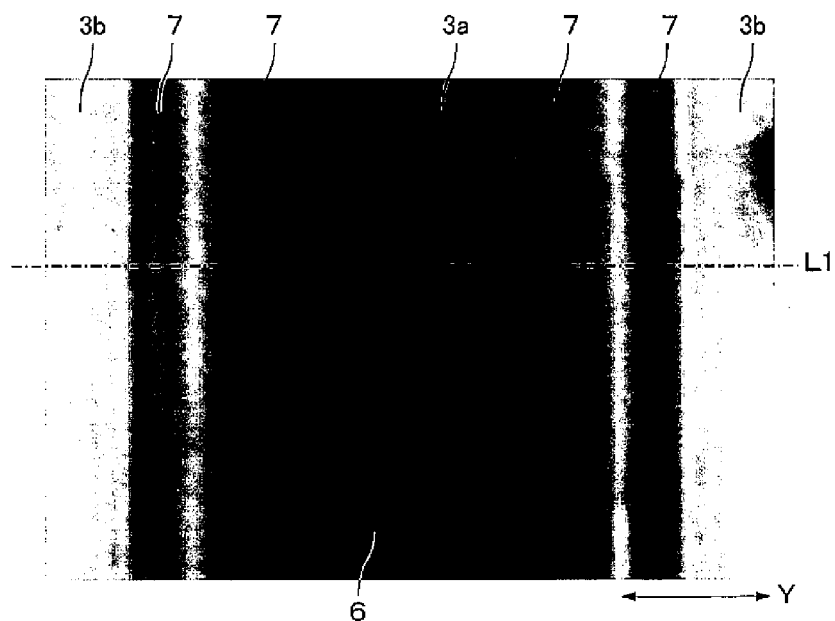
FIG. 8(a) is an enlarged view showing an image of the passage region of an extended layer and a portion near the passage region in a state in which a liquid sample is extended on the test piece used for a liquid sample analyzing method according to the prior art.
Figure 8B:
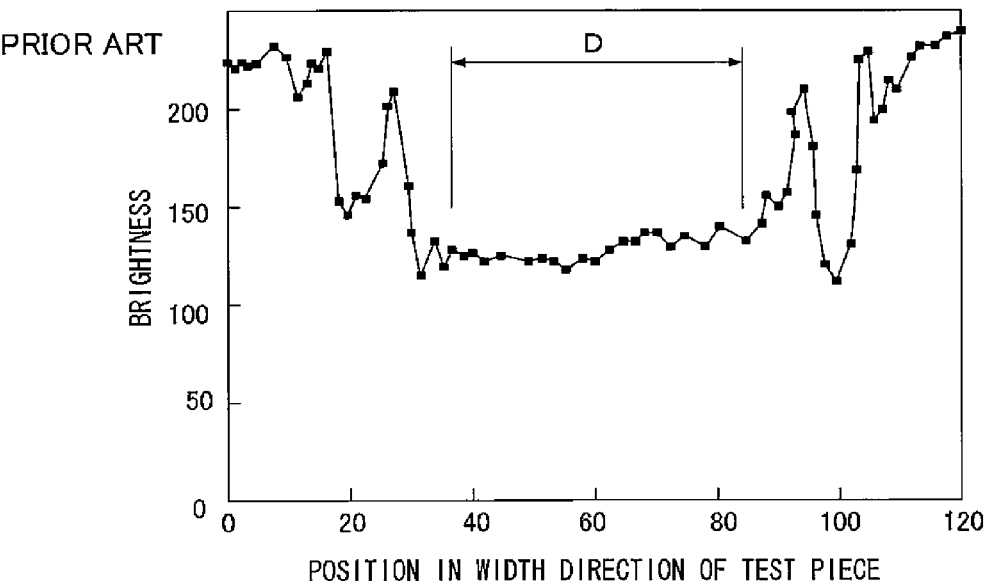
FIG. 8(b) shows brightness on a scanning line L1 at a corresponding point in the liquid sample analyzing method according to the prior art.

As shown in FIG. 2, the liquid sample analyzing apparatus 10 used for the liquid sample analyzing method according to the first embodiment of the present invention basically has the same constituent elements as in the liquid sample analyzing apparatus 10' of FIGS. 6 and 7. To be specific, the liquid sample analyzing apparatus 10 includes: a holder 11 that holds the test piece 1 placed on the holder 11; a light source 12 that emits light to the test piece 1 and is made up of, e.g., a lamp, a light-emitting diode, or a semiconductor laser; a diaphragm 13 that limits scattered light (transmitted light or reflected light) from the light source 12; a condenser lens 14 that focuses light having passed through the diaphragm 13; an image element 15 such as a CCD on which the light is focused to form an image of the surface of the test piece 1; and a control unit (not shown) that converts an electric signal from the image element 15 into a digital signal, performs processing such as image processing to calculate as an absorbance the degree of coloring (brightness) of the immobilized reagent portion 6 provided as a colored portion on the test piece 1, calculates the concentration of a target analyte in the liquid sample by using the absorbance according to a stored concentration conversion formula, and outputs the concentration. The diaphragm 13, the condenser lens 14, and the image element 15 constitute an optical system but the present invention is not limited to this configuration. Since the image element 15 such as a CCD is used, it is possible to remove a colored portion (color development) in the background of the extended layer 3 of the test piece 1 by a subtraction and increase the accuracy of measurement by correcting the coloring through color tone correction.

In the liquid sample analyzing apparatus 10 of the present invention, however, at the recognition of the width of the passage region 3a serving as the extended layer 3 (that is, the passage width), the control processing of the control unit is different from that of the prior art technique. In the present invention, the brightness of the test piece 1 is optically measured so as to cross the passage region 3a of the extended layer 3 and the overflow blocking lines 7, before the liquid sample is extended in the passage region 3a of the extended layer 3. The brightness is not measured after the liquid sample is extended in the passage region 3a of the extended layer 3. Based on brightness measurement data, the width of the passage region 3a of the extended layer 3 is decided.

To be specific, first, the test piece 1 is fixed on the holder 11 to be retained on the holder 11. In this state, pixels are scanned (scanning line L) so as to cross the passage region 3a of the extended layer 3 and the overflow blocking lines 7 on an image captured by the image element 15 and the width of the passage region 3a of the extended layer 3 is decided, before the liquid sample is extended in the passage region 3a of the extended layer 3, that is, before the liquid sample is added to the added portion 4 or before the added liquid sample reaches a measurement point, which will be described later, in the passage region 3a of the extended layer 3.

On the scanning line L in the passage region 3a of the extended layer 3 in a state in which the liquid sample is not extended, the provision of the labeled reagent portion 5 and the immobilized reagent portion 6 does not fluctuate brightness relative to the other passage region 3a. Thus brightness may be measured at any points in the passage region 3a of the extended layer 3 and pixels may be scanned at the immobilized reagent portions 6 in the passage region 3a of the extended layer 3. However, when the brightness may fluctuate relative to the other passage region 3a because of the provision of the labeled reagent portion 5 and the immobilized reagent portion 6, fluctuations in brightness may cause false recognition of a boundary portion. Thus in order to prevent such problems, it is preferable to scan pixels at points where the labeled reagent portion 5 and the immobilized reagent portions 6 are not provided in the passage region 3a of the extended layer 3.

Figure 3A:
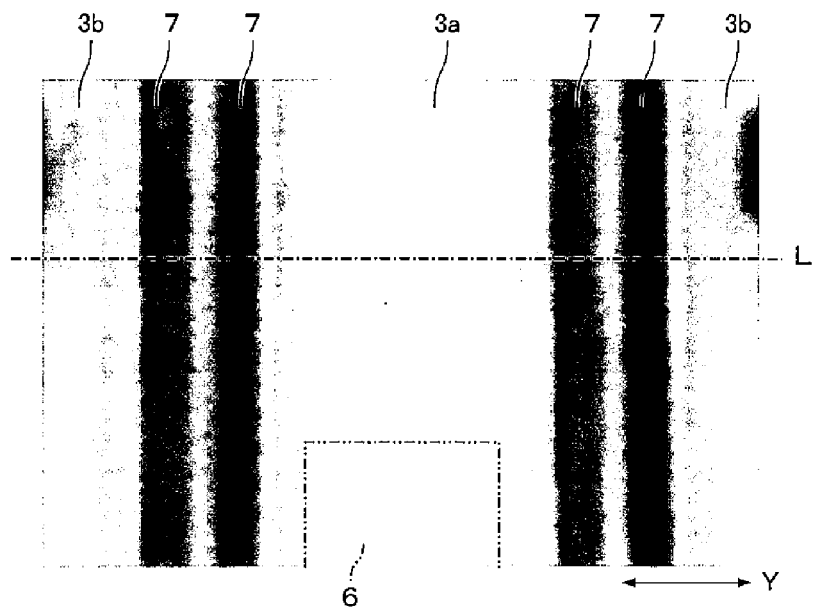
FIG. 3(a) is an enlarged view showing an image of the passage region of an extended layer and a portion near the passage region in a state in which a liquid sample is not extended on the test piece used for the liquid sample analyzing method according to the first embodiment of the present invention.
Figure 3B:
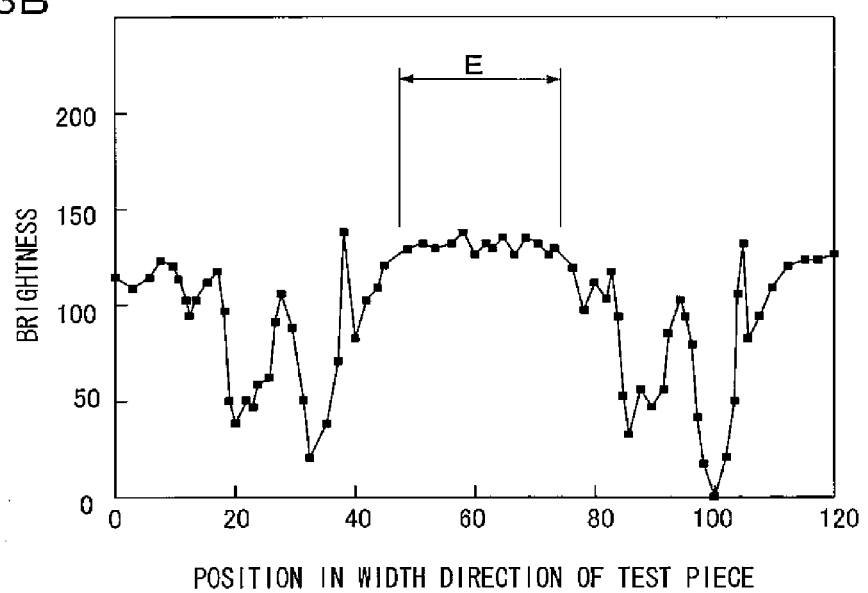
FIG. 3(b) shows brightness on a scanning line L at a corresponding point in the liquid sample analyzing method according to the first embodiment of the present invention.
Figure 4:
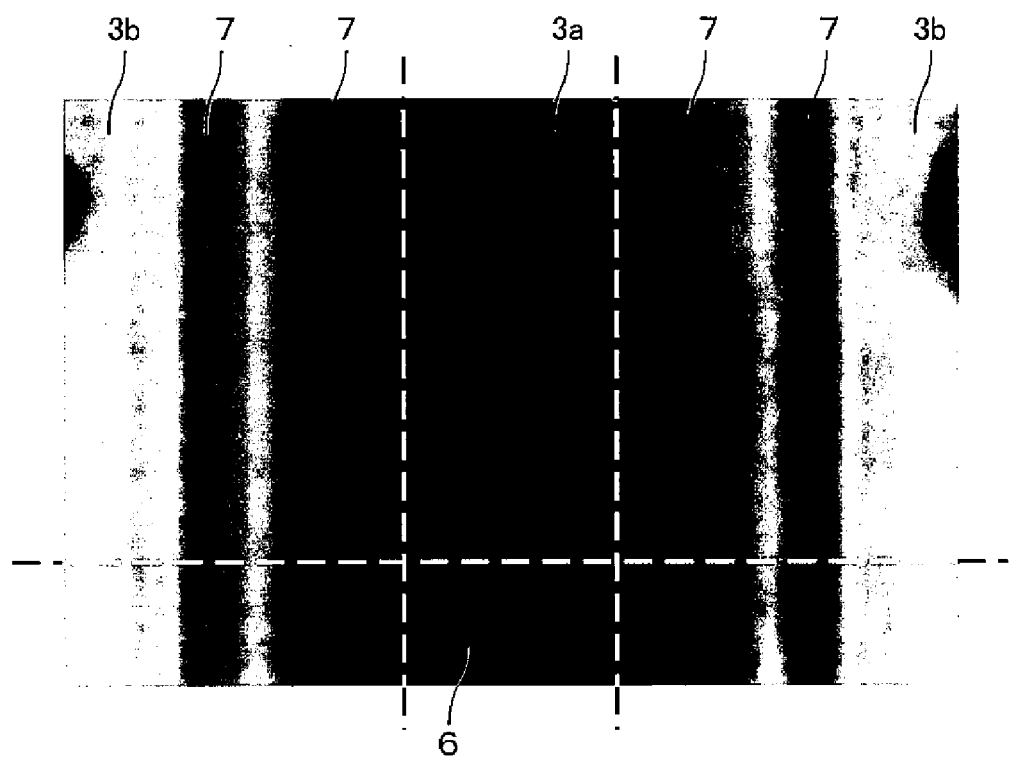
FIG. 4 is an enlarged view showing an image of the passage region of the extended layer and the portion near the passage region in a state in which the liquid sample is extended on the test piece used for the liquid sample analyzing method according to the first embodiment of the present invention.
Figure 5A:
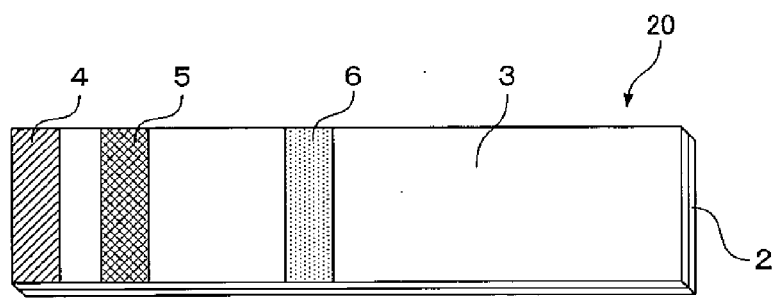
FIG. 5(a) is a perspective view showing a test piece having no overflow blocking lines according to the prior art.
Figure 5B:
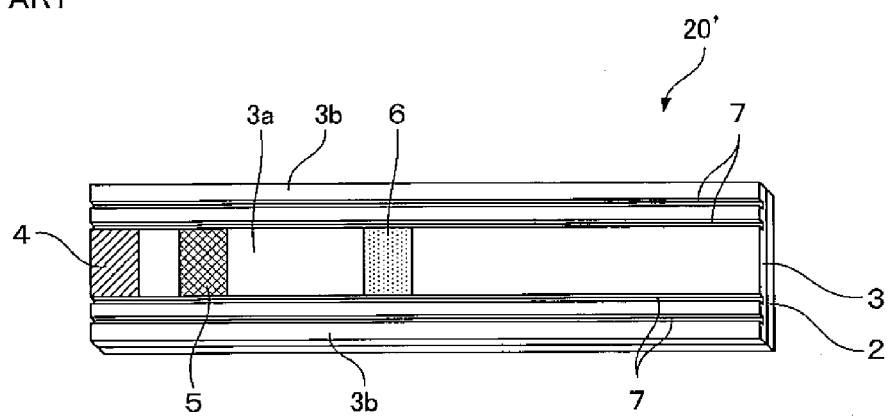
FIG. 5(b) is a perspective view showing a test piece having overflow blocking lines according to the prior art.

As shown in FIGS. 3(a) and 3(b), in a state in which the liquid sample is not extended in the passage region 3a of the extended layer 3, a difference in brightness is large at the boundary portion between the passage region 3a of the extended layer 3 and the overflow blocking line 7 (the brightness of the passage region 3a of the extended layer 3 is higher than that of the overflow blocking line 7). Thus a brightness fluctuation threshold value for recognizing the boundary portion between the passage region 3a of the extended layer 3 and the overflow blocking line 7 is stored beforehand in the storage of the control unit. In the passage region 3a of the extended layer 3 of the test piece 1, a recognized boundary portion is, for example, a portion where fluctuations in brightness reach at least a predetermined threshold value relative to a distance of movement in the width direction, or a portion where fluctuations in brightness reach at least the predetermined threshold value relative to the center of the passage region 3a in the width direction. Thus, a part inside the boundary portions can be reliably recognized as the passage region 3a of the extended layer 3 of the test piece 1.

After that, the holes 8 partially formed in the non-passage regions 3b of the extended layer 3 of the test piece 1 are detected by image processing, so that the positions of the immobilized reagent portions 6 are detected in the longitudinal direction of the test piece 1. The positions of the holes 8 may be detected by pattern matching on an image binarized by a proper threshold value. Instead of providing marks such as the holes 8 for recognizing the positions of the immobilized reagent portions 6 in the longitudinal direction of the test piece, the positions of the immobilized reagent portions 6 may be recognized in the longitudinal direction of the test piece based on, e.g., a distance from one end of the test piece 1. Further, the positions of the immobilized reagent portions 6 may be recognized in the longitudinal direction of the test piece before the recognition of the width of the passage region 3a of the extended layer 3.

In this way, regions where the immobilized reagent portions 6 are provided are correctly recognized based on the passage width decision information of the extended layer 3 and the test piece longitudinal position information of the immobilized reagent portions 6. After that, in a state in which the liquid sample is extended to the immobilized reagent portions 6 and is colored therein, coloring is measured in the immobilized reagent portions 6 that have been located. The coloring is converted to the concentration of the target analyte and the analysis result is outputted. The present invention is not limited to this method. After a measurement of a wide region containing the immobilized reagent portions 6, measurement data at portions corresponding to the respective regions of the immobilized reagent portions 6 may be inputted as concentration measurement data.

According to this method, in a state in which the liquid sample is not extended in the passage region 3a of the extended layer 3, the test piece 1 is measured so as to cross the passage region 3a of the extended layer 3 and the overflow blocking lines 7. The boundary portion can be properly recognized in a state in which a difference in brightness is large between the passage region 3a of the extended layer 3 and the overflow blocking line 7. It is therefore possible to properly set the passage width of the extended layer 3 and the measurement ranges of the immobilized reagent portions 6, which serve as colored portions, in the width direction of the test piece. Since the immobilized reagent portions 6 serving as colored portions can be measured in the properly set measurement ranges, it is possible to improve the reliability and accuracy of measurement.

In a state in which the liquid sample is not extended, the passage region 3a of the extended layer 3 and the overflow blocking lines 7 are colored substantially as in product shipment and the brightness of the extended layer 3 of the test piece 1 is stabilized. It is therefore possible to properly and relatively easily set the brightness fluctuation threshold value that is a criterion for distinguishing between the passage region 3a of the extended layer 3 and the overflow blocking line 7. Consequently, it is possible to correctly and quickly recognize the boundary portion between the passage region 3a of the extended layer 3 and the overflow blocking line 7, so that high reliability can be kept and the time of recognition can be reduced. Further, the passage region 3a of the extended layer 3 is substantially uniformly colored in the width direction during measurement. Thus it is possible to properly recognize the width of the passage region 3a of the extended layer 3, improving the reliability and accuracy of measurement.

In the present embodiment, the regions of the immobilized reagent portions 6 of the test piece 1 are recognized in the longitudinal direction of the test piece 1 by using the holes 8 and a distance from the end of the test piece 1. The present invention is not limited to this method. The regions of the immobilized reagent portions 6 of the test piece 1 may be recognized in the longitudinal direction of the test piece based on variations in concentration (fluctuations in brightness) in a state in which the immobilized reagent portions 6 are colored.

In the present embodiment, the overflow blocking lines 7 are formed by partially melting and hardening the extended layer 3, which contains the porous carrier, with laser light emitted to the extended layer 3. The present invention is not limited to this configuration. The present invention is also applicable to a test piece on which liquid impermeable partition members are linearly provided to prevent a liquid sample from flowing to the outside.

Second Embodiment

The following will describe, as a second embodiment, a displacement correcting method of a test piece in the liquid sample analyzing method of the first embodiment. The displacement correcting method is not always performed concurrently with the liquid sample analyzing method of the first embodiment in which pixels are scanned so as to cross the passage region and the overflow blocking lines. The displacement correcting method is also applicable to a typical liquid sample analyzing method of the prior art.

FIGS. 9, 10, 11(a), 11(b), 12, 13, and 14 show a test piece 1 and a measuring device of the test piece 1 according to the second embodiment.

Figure 20:
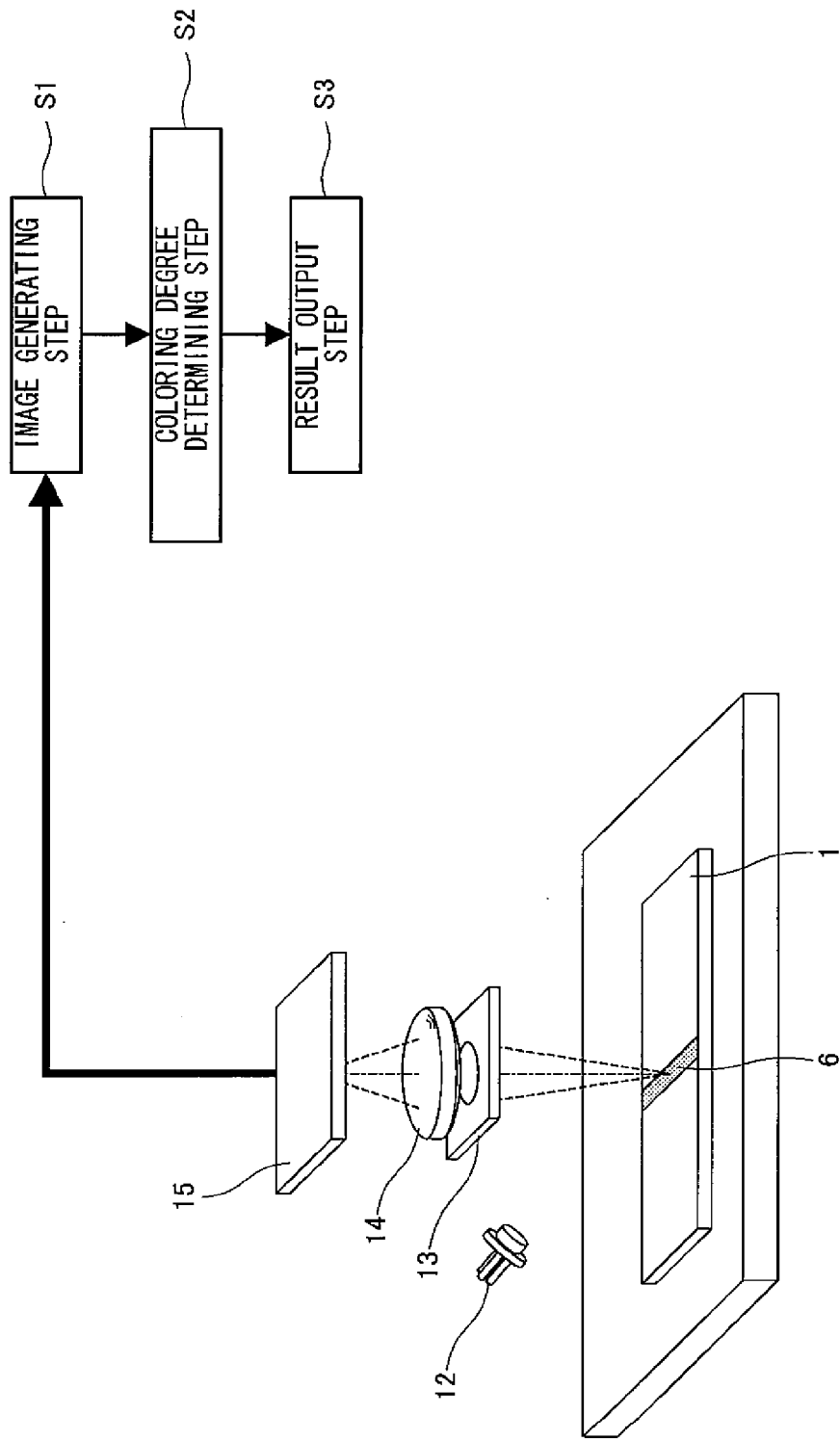
FIG. 20 is a structural diagram of a measuring method using the test piece of the prior art.

The second embodiment is different from the prior art of FIG. 20 in that a reference mark 23 including a hole 8 (see FIG. 1) is added to a part of the test piece 1 and the method further includes reference mark detecting step S1-a and test piece displacement correcting step S1-b.

The specific configuration of the test piece 1 is also different from the prior art configuration of FIG. 20 and will be described later. The same configurations as those of FIG. 20 are indicated by the same reference numerals and the explanation thereof is omitted.

The test piece 1 disposed on a holder 11 is irradiated by a light source 12 and is photographed by an optical system including a diaphragm 13, a condenser lens 14, and an image element 15. In reference mark detecting step S1-a following image generating step S1, the position of the reference mark 23 is detected from a gray image generated in image generating step S1.

In test piece displacement correcting step S1-b, image processing is performed on the gray image to correct a displacement of the test piece.

Figure 10:
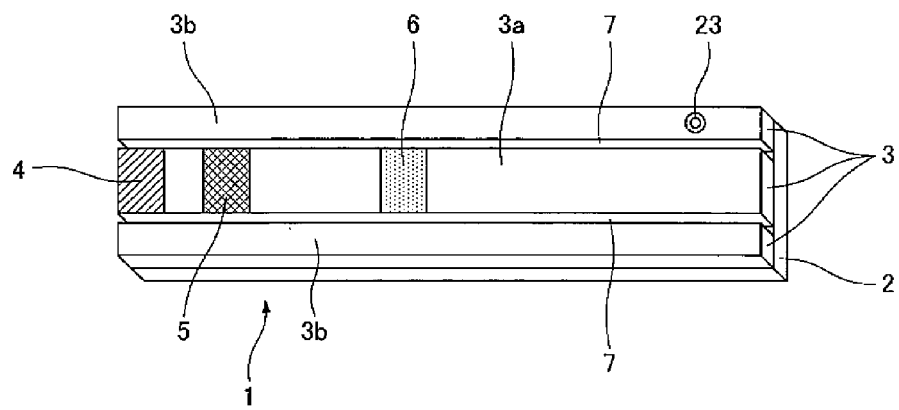
FIG. 10 is a structural diagram showing the test piece according to the second embodiment.

The test piece 1 of the present embodiment is configured as shown in FIG. 10.

On the test piece 1, an extended layer 3 is divided into a central passage region 3a and non-passage regions 3b by two overflow blocking lines 7, and the reference mark 23 is disposed in the non-passage region 3b. The reference mark 23 is formed at a position based on a relative positional relationship with an immobilized reagent portion 6. To be specific, the reference mark 23 is formed at the specified position that is separated from the specific position of the immobilized reagent portion 6 by specified distances respectively in X-axis direction and Y-axis direction.

The extended layer 3 contains a porous carrier of nitrocellulose as in the prior art. A support 2 is a liquid impermeable sheet of polyethylene terephthalate. The extended layer 3 is 0.25 mm in thickness and the support 2 is 0.5 mm in thickness. The reference mark 23 is formed of a through hole penetrating the extended layer 3 and the support 2.

The through hole of the reference mark 23 is formed by melting the extended layer 3 and the support 2 with $CO_2$ laser that is emitted by a $CO_2$ laser marker perpendicularly to the surface of the extended layer 3 with a constant output for a certain period of time. The through hole 3 formed by this method is shown in FIGS. 11(a) and 11(b).

Figure 11A:
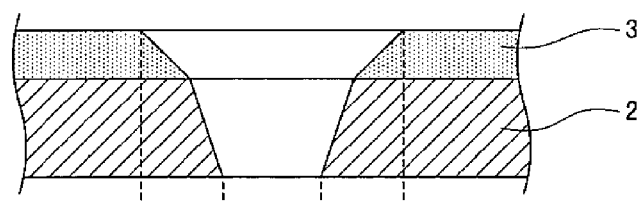
FIG. 11(a) is an enlarged sectional view showing a reference mark according to the second embodiment.
Figure 11B:
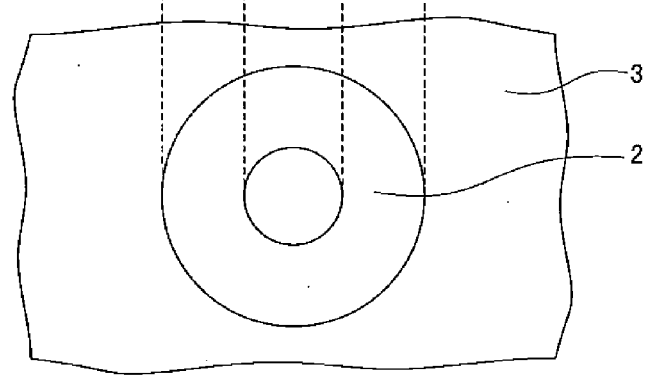
FIG. 11(b) is a plan view showing the reference mark according to the second embodiment.

FIG. 11(a) is a sectional view of the reference mark 23. The reference mark 23 has a diameter of about 0.6 mm at the extended layer 3 and has a diameter of about 0.3 mm at the support 2. This is because nitrocellulose of the extended layer 3 is more subject to thermal melting than polyethylene terephthalate of the support 2. FIG. 11(b) is a plan view of the reference mark 23 from the extended layer 3. As shown in FIG. 11(b), the reference mark 23 has two circular edges.

The holder 11 on which the test piece 1 with the reference mark 23 is placed has a surface painted darker than the extended layer 3 and the support 2. To be specific, the extended layer 3 and the support 2 are white and the surface of the holder 11 is painted black.

Figure 13:
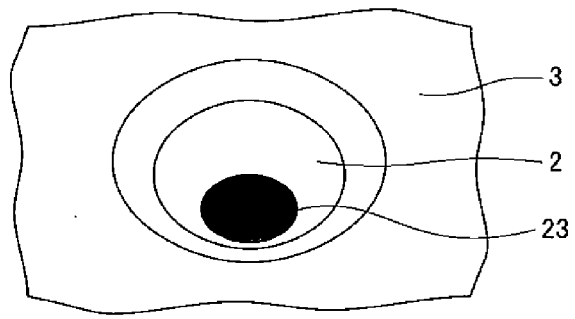
FIG. 13 shows a partial image around the reference mark according to the second embodiment.
Figure 14:
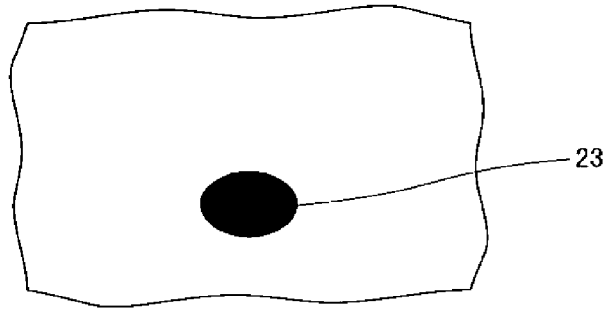
FIG. 14 is a binary image around the reference mark according to the second embodiment.

When a gray image is captured on the image element 15 in a state in which the test piece 1 is disposed on the holder 11, the reference mark 23 looks black like the holder 11 as shown in FIG. 13. Since the extended layer 3 and the support 2 are white, as shown in FIG. 13, the gray image cut around the reference mark 23 is a partial image containing the reference mark 23 with a high contrast.

In reference mark detecting step S1-a, the partial image is used to determine a displacement pre-correction reference mark position that indicates the position of the reference mark 23 on the gray image.

Figure 12:
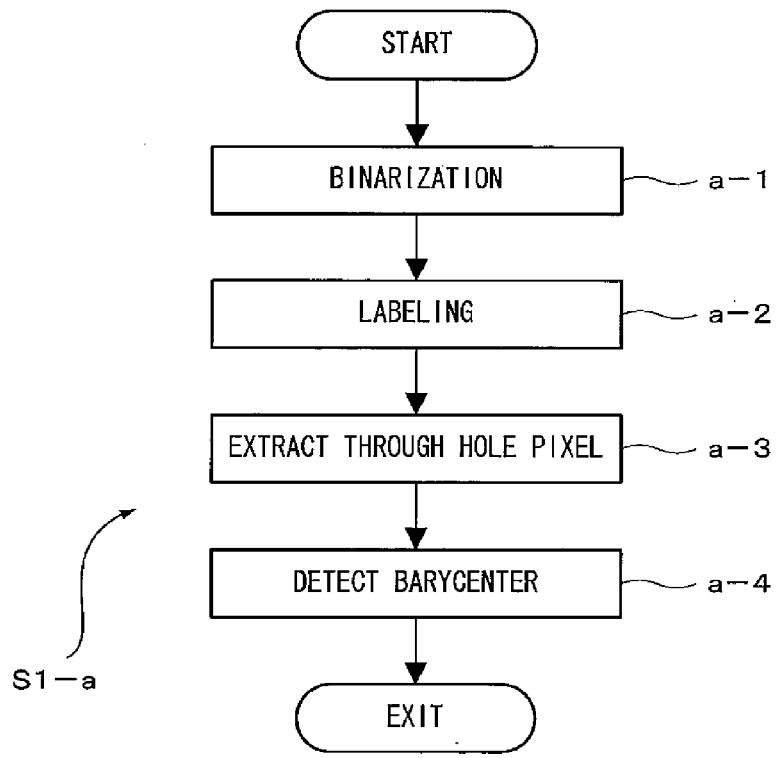
FIG. 12 is a flowchart for explaining the steps of determining a displacement pre-correction reference mark according to the second embodiment.

Referring to FIG. 12, the following will describe the steps of determining the displacement pre-correction reference mark position.

FIG. 12 shows a flowchart for explaining the steps of determining the displacement pre-correction reference mark position according to the second embodiment.

In step a-1, the partial image is thresholded by a predetermined threshold value to form a binary image. The partial image of FIG. 13 is thresholded by the predetermined threshold value, generating the binary image of FIG. 14. In this case, the predetermined threshold value is 100 relative to a range of 0 to 255.

In step a-2, the binary image generated in step S1 is subjected to labeling to extract the connected components of black pixels. In the example of the binary image of FIG. 14, only one connected component of black pixels corresponds to the through hole. In some cases, other connected components may appear because of dust on the extended layer 3 and noise from the image element 15.

In step a-3, the feature parameters of the extracted connected components are examined and one of the connected components is extracted such that the extracted component matches the characteristics of the through hole. The feature parameters of the connected components are numeric values indicating the shape of an object, e.g., the area, the circularity, and the circumference of the object. In the simplest method, an area range may be determined by measuring the area of the connected component of black pixels corresponding to the through hole.

Next, in step a-4, the barycentric coordinates of the connected component of the through hole are determined. Barycentric coordinates in the binary image can be determined as the mean values of the X and Y coordinates of all pixels constituting the connected component. The detected barycentric coordinates are used as the displacement pre-correction reference mark position of the reference mark 23.

Through steps a-1 to a-4, the displacement pre-correction reference mark position of the reference mark 23 is determined.

Next, in test piece displacement correction step S1-*b*, the gray image generated in image generating step S1 is translated such that the displacement pre-correction reference mark position determined in reference mark detecting step S1-*a* is aligned with a predetermined displacement post-correction reference mark position. Thus a displacement of the test piece 1 can be corrected.

As has been discussed, in the second embodiment, the reference mark 23 is provided in the non-passage region 3*b* of the test piece 1, so that a displacement of the test piece is corrected by image processing. Further, the range of the immobilized reagent portion 6 is correctly recognized in colored portion determining step S2, thereby improving the accuracy of measurement. Moreover, a displacement is corrected by the liquid sample analyzing method of the first embodiment, so that it is possible to properly set the passage width of the extended layer 3 and the measurement range of the immobilized reagent portion 6, which serves as a colored portion, in the width direction of the test piece. Since a displacement of the test piece 1 can be corrected, it is possible to improve the reliability and accuracy of measurement of the colored portion.

The reference mark 23 is shaped like a through hole as shown in FIG. 11 and the holder 11 is colored black. Thus it is possible to increase the contrast of the reference mark on the gray image in reference mark detecting step S1-*a*, obtain an excellent binary image, and improve the detection accuracy of the reference mark.

The extended layer 3 is divided into the passage region 3*a* and the non-passage regions 3*b* by the overflow blocking lines 7. The present invention is not limited to this configuration.

Third Embodiment

Figure 15A:
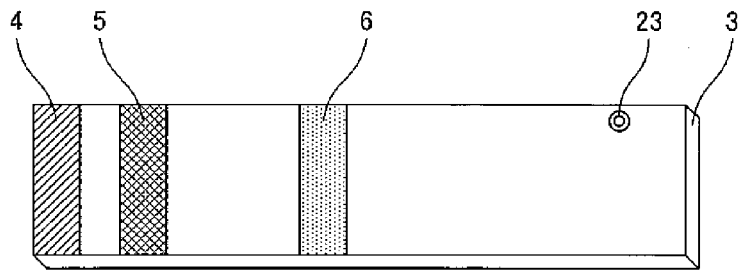
FIG. 15(a) is another structural diagram showing a test piece according to a third embodiment of the present invention.
Figure 15B:
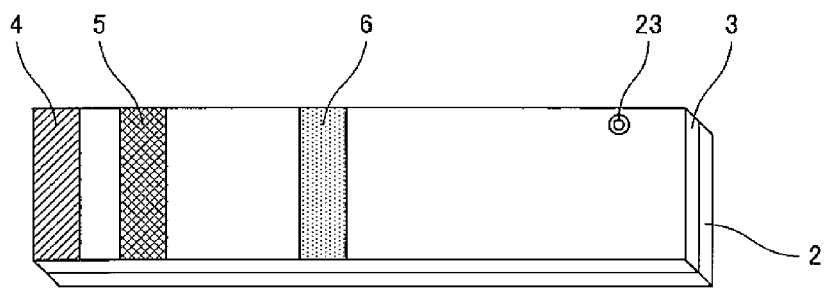
FIG. 15(b) is another structural diagram showing a test piece according to the third embodiment of the present invention.
Figure 15C:
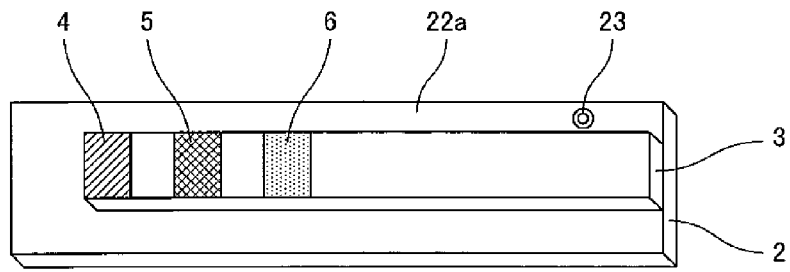
FIG. 15(c) is another structural diagram showing a test piece according to the third embodiment of the present invention.

FIGS. 15(*a*), 15(*b*), and 15(*c*) show other specific examples of a test piece 1.

In the test piece 1 of FIG. 15(*a*), the support 2 of the test piece 1 according to the second embodiment is not provided. The test piece 1 of FIG. 15(*a*) is different from the test piece 1 of FIG. 10 in that a reference mark 23 is a through hole penetrating only an extended layer 3, overflow blocking lines 7 are not provided, and the overall extended layer 3 serves as a passage region.

By combining the test piece 1 configured thus with a holder 11 painted dark, a gray image of the reference mark 23 can be obtained as shown in FIG. 13. Thus the present invention is applicable to the test piece 1 of FIG. 15(*a*).

A test piece 1 of FIG. 15(*b*) is different from the test piece 1 of FIG. 10 in that the overflow blocking lines 7 of the test piece 1 according to the second embodiment are not provided and an overall extended layer 3 serves as a passage portion. A reference mark 23 is a through hole penetrating the extended layer 3 and a support 2.

By combining the test piece 1 configured thus with the holder 11 painted black, a gray image of the reference mark can be obtained as shown in FIG. 13. Thus the present invention is applicable to the test piece 1 of FIG. 15(*b*).

A test piece 1 of FIG. 15(*c*) is different from the test piece 1 of FIG. 10 in that the non-passage regions 3*b* of the test piece 1 according to the second embodiment are not provided and a support 2 is partially exposed.

To be specific, the support 2 covers the opposite surface of an extended layer 3 from an immobilized reagent portion 6 contained in the other surface of the extended layer 3 and the support 2 has an exposed portion 22*a* near the extended layer 3. A reference mark 23 is a through hole that is provided on the exposed portion 22*a* of the support 2 and penetrates only the support 2.

By combining the test piece 1 configured thus with the holder 11 painted black, a gray image of the reference mark can be obtained as shown in FIG. 13. Thus the present invention is applicable to the test piece 1 of FIG. 15(*c*).

In these examples, the overflow blocking lines are not formed on the test piece. The present invention is similarly applicable to a test piece including at least one pair of overflow blocking lines 7.

A displacement is corrected thus by the liquid sample analyzing method of the first embodiment. It is therefore possible to properly set the passage width of the extended layer 3 and the measurement range of an immobilized reagent portion 6, which serves as a colored portion, in the width direction of the test piece. Since a displacement of the test piece 1 can be corrected, it is possible to improve the reliability and accuracy of measurement of the colored portion.

Fourth Embodiment

Figure 16A:
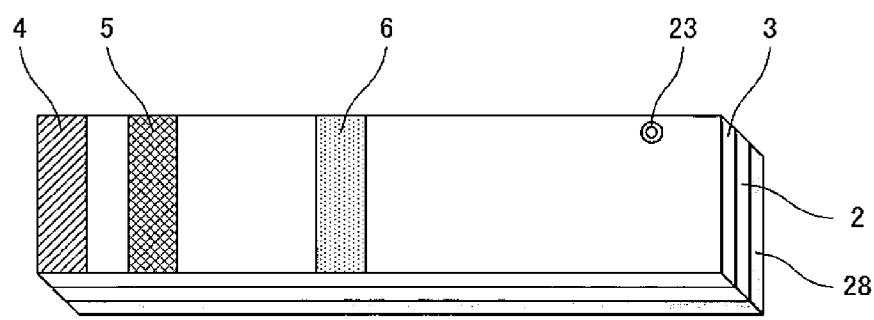
FIG. 16(a) is another structural diagram showing a test piece according to a fourth embodiment of the present invention.
Figure 16B:
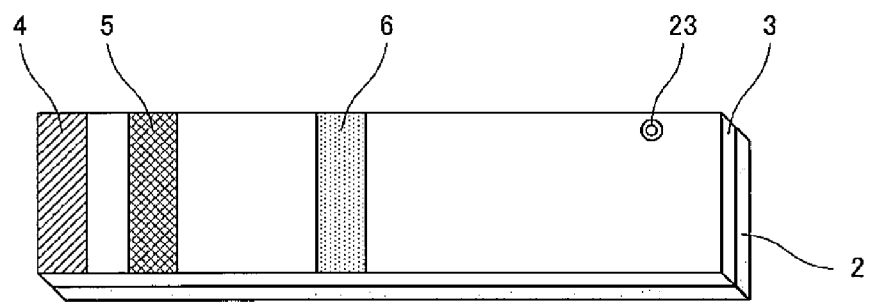
FIG. 16(b) is another structural diagram showing a test piece according to the fourth embodiment of the present invention.

FIGS. 16(*a*) and 16(*b*) show other specific examples of a test piece 1.

In the test piece 1 of the third embodiment in FIG. 15, the holder 11 is painted dark to increase the contrast of a gray image of the reference mark 23, whereas in test pieces 1 of FIGS. 16(*a*) and 16(*b*), regardless of the color of a holder 11, a gray image of a reference mark can be obtained with a high contrast as shown in FIG. 13.

Figure 17A:
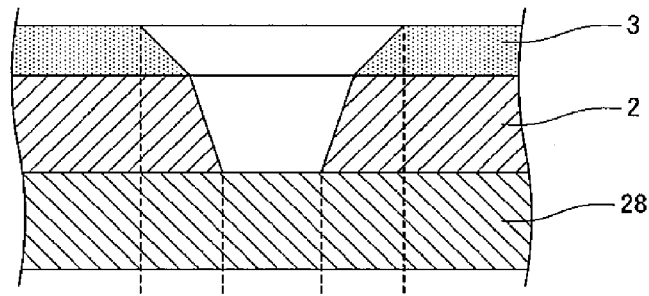
FIG. 17(a) is an enlarged sectional view showing a reference mark according to the fourth embodiment.
Figure 17B:
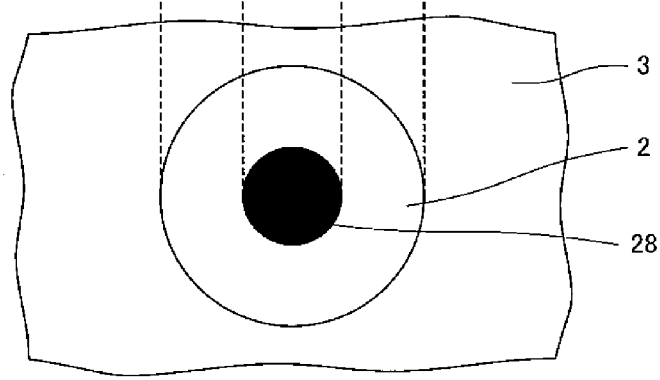
FIG. 17(b) is a plan view showing the reference mark according to the fourth embodiment.

The test piece 1 of FIG. 16(*a*) is different from the test piece of FIG. 10 in that no overflow preventing lines 7 are provided, an overall extended layer 3 serves as a passage region, and a light shielding layer 28 of dark color such as black is provided under a support 2. FIGS. 17(*a*) and 17(*b*) are a sectional view and a plan view of a reference mark 23 of the test piece 1. As shown in the sectional view of FIG. 17(*a*), the reference mark 23 is a hole penetrating the extended layer 3 and the support 2. As shown in the plan view of FIG. 17(*b*), the light shielding layer 28 is exposed as a black portion. Thus regardless of the painted color of the holder 11, a gray image of the reference mark can be obtained as shown in FIG. 13, so that the present invention is applicable to the test piece 1 of FIG. 16(*a*).

Figure 18A:
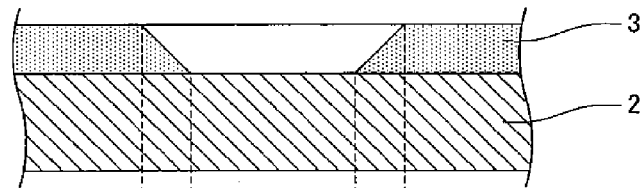
FIG. 18(a) is an enlarged sectional view showing a reference mark according to the fourth embodiment.
Figure 18B:
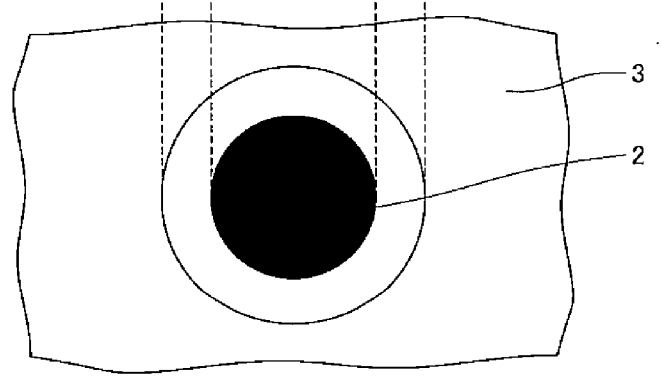
FIG. 18(b) is a plan view showing the reference mark according to the fourth embodiment.

The test piece 1 of FIG. 16(*b*) is different from the test piece of FIG. 10 in that no overflow preventing lines 7 are provided, an overall extended layer 3 serves as a passage region, and a support 2 also acts as a light shielding layer that is painted darker than the surface of the extended layer 3, to be specific, the support 2 is painted black. FIGS. 18(*a*) and 18(*b*) are a sectional view and a plan view of a reference mark 23. As shown in the sectional view of FIG. 18(*a*), the reference mark 23 is a hole penetrating only the extended layer 3. In the test piece configured thus, as shown in the plan view of FIG. 18(*b*), the support 2 is exposed as a black portion. Thus regardless of the painted color of the support 11, a gray image of the reference mark can be obtained as shown in FIG. 13, so that the present invention is applicable to the test piece 1 of FIG. 16(*b*).

In these examples, the overflow blocking lines are not formed on the test piece. The present invention is similarly applicable to a test piece including at least one pair of overflow blocking lines 7.

A displacement is corrected thus by the liquid sample analyzing method of the first embodiment. Thus it is possible to properly set the passage width of the extended layer 3 and the measurement range of an immobilized reagent portion 6, which serves as a colored portion, in the width direction of the test piece. Since a displacement of the test piece 1 can be corrected, it is possible to improve the reliability and accuracy of measurement of the colored portion.

Fifth Embodiment

Figure 19:
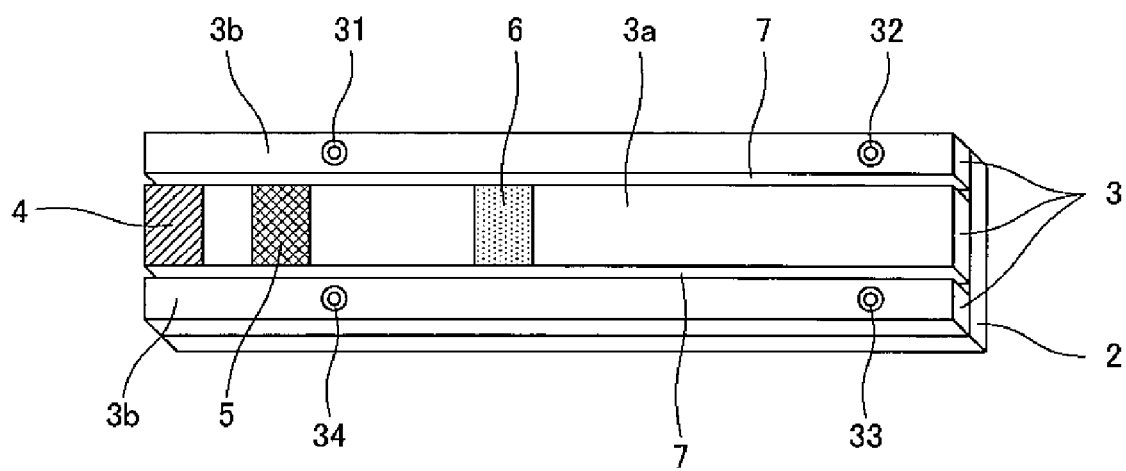
FIG. 19 is a structural diagram showing a test piece according to a fifth embodiment of the present invention.

FIG. 19 shows another specific example of a test piece 1.

In the second embodiment, the reference mark 23 is provided only at a single point and only a parallel displacement is corrected. By providing reference marks at multiple points, it is possible to correct not only a parallel displacement but also displacements such as rotation and scaling.

FIG. 19 shows a test piece 1 on which the reference marks 23 of the second to fourth embodiments are provided at multiple points. Instead of the reference marks 23 on the test piece of FIG. 10, reference marks 31, 32, 33, and 34 are provided at four points.

In the case of the multiple reference marks, in reference mark detecting step S1-a, the positions of the reference marks are determined by the steps of the flowchart of FIG. 12. In test piece displacement correcting step S1-b, a gray image generated in image generating step S1 is translated, rotated, and scaled up or down such that the positions of the reference marks are aligned with the predetermined displacement post-correction reference mark positions of respective displacement pre-correction reference mark positions, so that a displacement of the test piece 1 can be corrected.

The image can be translated, rotated, and scaled up or down by performing linear coordinate transformation, which is generally known as affine transformation, on the gray image.

In the foregoing embodiments, the holder 11 is black and the extended layer 3 and the support 2 are white. The combination of colors is not particularly limited as long as a high contrast is obtained between the center and other regions of the reference mark.

Preferably, the multiple reference marks are disposed as the vertexes of a two-dimensional figure having no symmetry axes. Further, the multiple reference marks are preferably disposed as the vertexes of a two-dimensional figure having no points of symmetry. In other words, the reference marks are formed at asymmetric positions with respect to a center line parallel to the extension direction of the extended layer, a central point, or both of the center line and the central point, so that incorrect mounting of the test piece can be detected, for example, when the test piece is erroneously flipped or turned around.

Figure 21A:
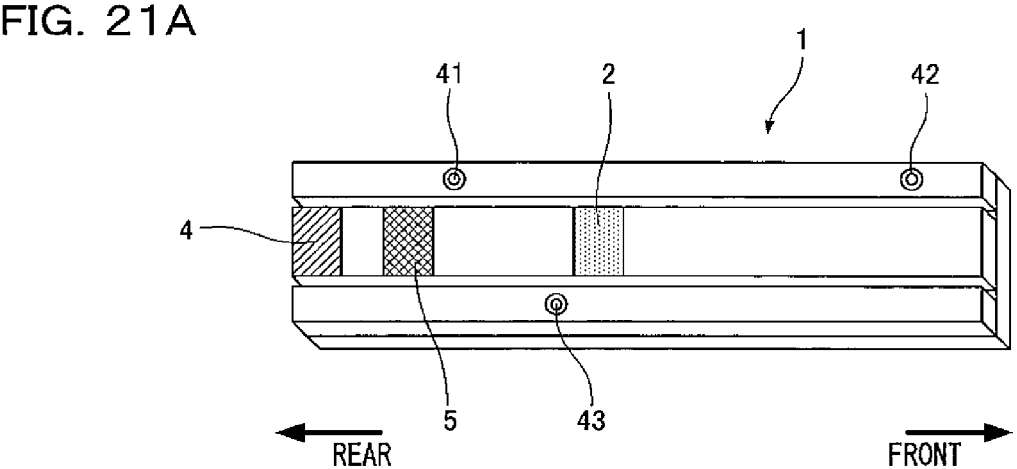
FIG. 21(a) is a structural diagram showing a test piece having asymmetric reference marks according to the fifth embodiment of the present invention.
Figure 21B:
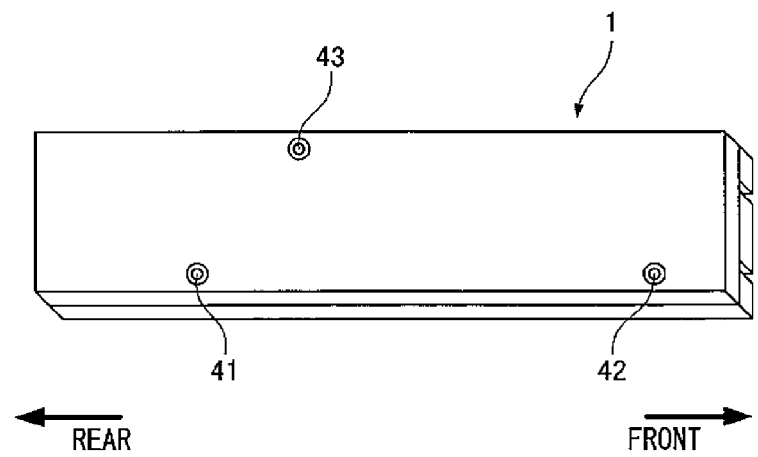
FIG. 21(b) is a structural diagram showing the test piece having the asymmetric reference marks according to the fifth embodiment of the present invention.

FIGS. 21(a) and 21(b) are structural diagrams showing a test piece including asymmetric reference marks according to a fifth embodiment of the present invention. FIG. 21(a) is a front view and FIG. 21(b) is a rear view.

In FIGS. 21(a) and 21(b), reference marks 41, 42, and 43 are through holes penetrating to the back side.

As shown in the structural diagram of FIG. 9, a test piece 1 is mounted on a holder 11. The test piece 1 may be erroneously flipped, turned around, or may be flipped and turned around on the holder 11. Further, the test piece 1 may be mounted on the holder 11 while being inserted with an improper depth.

When the test piece 1 is incorrectly mounted thus, correct measurement cannot be achieved.

Figure 22:
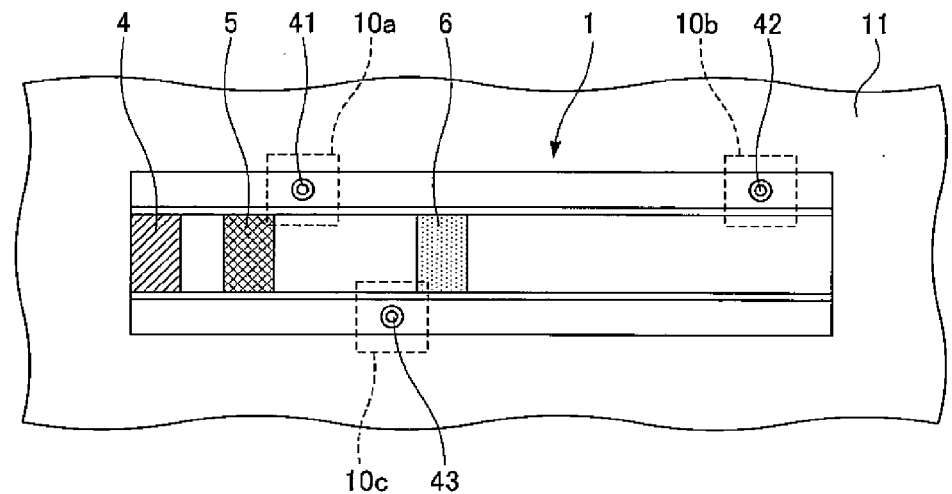
FIG. 22 shows the correctly mounted test piece according to the fifth embodiment.
Figure 23:
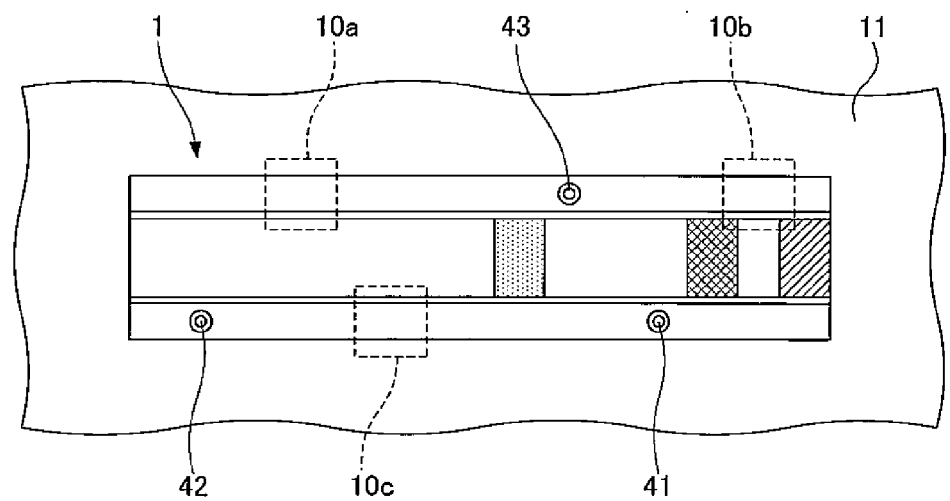
FIG. 23 shows that the test piece is turned around and mounted according to the fifth embodiment.

FIG. 22 shows the correctly mounted test piece according to the fifth embodiment. FIG. 23 shows that the test piece is turned around and mounted according to the fifth embodiment. FIG. 24 shows that the test piece is flipped and mounted according to the fifth embodiment. FIG. 25 shows that the test piece is mounted after being flipped and turned around according to the fifth embodiment.

FIG. 22 shows that the test piece 1 is correctly mounted and is inserted with a proper depth.

In FIG. 23, the test piece 1 is inserted with a proper depth but is erroneously turned around.

In FIG. 24, the test piece 1 is erroneously flipped over and is inserted with an excessive depth.

In FIG. 25, the test piece 1 is erroneously flipped over and turned around with an excessive depth.

Further, reference mark searching ranges 10a, 10b, and 10c are provided each of which has a specific size at a specific position in an image. The reference mark searching ranges 10a to 10c correspond to the reference marks 41 to 43, respectively. When the test piece 1 is correctly mounted, the reference mark searching ranges 10a to 10c respectively contain the images of the reference marks 41 to 43. When incorrect mounting of flipping or turning is detected, the reference mark searching ranges 10a to 10c are desirably large enough to contain images displaced by the dimension errors of the test piece 1 and the holder 11. For example, the reference mark searching ranges are preferably rectangular and the length of one side of the reference mark searching range is preferably two to three times the diameter of the image of the reference mark.

The following will specifically describe a method of recognizing the mounting states of FIGS. 22 to 25.

First, it is decided whether or not the reference mark searching ranges 10a to 10c on an image contain the respective reference marks. The reference marks are confirmed as in the second to fourth embodiments.

When the reference mark searching ranges 10a to 10c contain the respective reference marks, it is decided that the test piece 1 is correctly mounted. FIG. 26 shows decision results on whether or not the reference mark searching ranges 10a to 10c contain the reference marks on the images of FIGS. 22 to 25. FIG. 26 shows the recognition patterns of the reference marks according to the fifth embodiment. According to the results, only in FIG. 22 where the test piece 1 is correctly mounted and inserted with a proper depth without being flipped or turned around, it is decided that the reference marks are present in the respective reference mark searching ranges 10a to 10c. This is because the reference marks 41 to 43 are not arranged with line symmetry or point symmetry.

When it is decided that the reference mark searching ranges 10a to 10c do not all contain the respective reference marks and the test piece 1 is incorrectly mounted, chromatography measurement is stopped and a warning is issued. When the reference mark searching ranges 10a to 10c contain the respective reference marks, the foregoing correction process is performed.

In the foregoing embodiments, the reference marks 41 to 43 are through holes. The reference marks 41 to 43 may be formed by printing. In the case of printing, the reference marks are printed not only on the front side but also on the back side of the test piece such that the reference marks are placed at the same positions as the openings of the through holes.

In this example, the three reference marks are provided. The number of reference marks is not limited as long as the reference marks are not arranged with line symmetry or point symmetry.

A displacement is corrected thus by the liquid sample analyzing method of the first embodiment. Thus it is possible to properly set the passage width of the extended layer 3 and the measurement range of the immobilized reagent portion 6, which serves as a colored portion, in the width direction of the test piece. Since a displacement of the test piece 1 can be corrected, it is possible to improve the reliability and accuracy of measurement of the colored portion.

In the foregoing explanation, the second to fifth embodiments are implemented concurrently with the first embodiment. These embodiments may be used only to correct a displacement of the test piece without recognizing the position of, e.g., the colored portion.

INDUSTRIAL APPLICABILITY

A liquid sample analyzing method according to the present invention is applicable to analyzing methods using various test pieces, wherein the test piece includes an extended layer for receiving a liquid sample and the extended layer includes a passage region divided by overflow blocking lines.

The invention claimed is:

1. A liquid sample analyzing method using a test piece,
the test piece comprising an extended layer on which a liquid sample is extended,
the extended layer comprising:
overflow blocking lines for preventing the liquid sample from flowing to an outside from a passage region of the extended layer; and
a colored portion that is provided on a part of the passage region of the extended layer and contains an immobilized reagent,
the analyzing method comprising:
extending the liquid sample added to the test piece, in the passage region of the extended layer; and
analyzing a target analyte in the liquid sample by optically detecting coloring of the colored portion,
wherein in a state in which the liquid sample is not extended in the passage region of the extended layer, the analyzing method further comprises:
optically measuring the test piece so as to cross the passage region of the extended layer and the overflow blocking lines; and
deciding a passage width of the extended layer based on measurement data.

2. The liquid sample analyzing method according to claim 1, wherein the passage width of the extended layer is decided by capturing an image containing the test piece on an image element and scanning pixels of the image so as to cross the passage region of the extended layer and the overflow blocking lines.

3. The liquid sample analyzing method according to claim 1, wherein the colored portion is measured or measurement information about the colored portion is inputted based on decision information about the passage width of the extended layer.

4. The liquid sample analyzing method according to claim 1, wherein the overflow blocking lines are formed by melting and hardening a part of the extended layer containing a porous carrier, with laser light emitted to the extended layer.

5. The liquid sample analyzing method according to claim 1, wherein the liquid sample added to the test piece is extended and measured by chromatography.

6. The liquid sample analyzing method according to claim 1, wherein the test piece includes at least one reference mark formed at a position relative to the colored portion, the at least one reference mark including a hole penetrating the extended layer from a surface containing the colored portion.

7. The liquid sample analyzing method according to claim 1, wherein the test piece comprises:

a support covering an opposite surface of the extended layer from the colored portion contained in an other surface of the extended layer; and
at least one reference mark that is a hole penetrating the extended layer and the support from the surface containing the colored portion.

8. The liquid sample analyzing method according to claim 1, wherein the test piece comprises:
a support that covers an opposite surface of the extended layer from the colored portion contained in an other surface of the extended layer and partially contains an exposed portion near the extended layer; and
a reference mark that is a hole penetrating the support from the exposed portion.

9. The liquid sample analyzing method according to claim 1, wherein the test piece comprises:
a light shielding layer that is bonded to the extended layer directly or via a support and is darker than a surface color of the extended layer; and
a reference mark that is a hole penetrating the extended layer from a surface containing the colored portion, the hole partially exposing the light shielding layer.

10. The liquid sample analyzing method according to claim 6, wherein the reference mark is a hole that is formed by laser melting and is circular in cross section along the surface containing the colored portion.

11. The liquid sample analyzing method according to claim 6, wherein the at least one reference mark comprises multiple reference marks formed at asymmetric positions with respect to a center line parallel to an extension direction of the extended layer and a central point.

12. The liquid sample analyzing method according to claim 6, wherein the at least one reference mark is a printed mark formed instead of the through hole, at a point corresponding to an opening of the through hole.

13. The liquid sample analyzing method according to claim 6, further comprising:
an image generating step of generating a gray image by imaging, with an image sensor, the surface containing the colored portion on the test piece before the optical measurement;
a reference mark detecting step of calculating, from the gray image, a displacement pre-correction reference mark position indicating a position of the at least one reference mark of the test piece; and
a sensor displacement correcting step of performing linear coordinate transformation on the gray image such that the displacement pre-correction reference mark position is aligned with a corresponding displacement post-correction reference mark position.

14. The liquid sample analyzing method according to claim 9, further comprising:
an image generating step of generating a gray image by imaging, with an image sensor, the surface containing the colored portion on the test piece before the optical measurement;
a reference mark detecting step of calculating, from the gray image, a displacement pre-correction reference mark position indicating a position of the reference mark of the test piece; and
a sensor displacement correcting step of performing linear coordinate transformation on the gray image such that the displacement pre-correction reference mark position is aligned with a corresponding displacement post-correction reference mark position.

15. The liquid sample analyzing method according to claim 11, further comprising:

an image generating step of generating a gray image by imaging, with an image sensor, the surface containing the colored portion on the test piece before the optical measurement;

a reference mark detecting step of calculating, from the gray image, displacement pre-correction reference mark positions indicating positions of the reference marks of the test piece;

an incorrect mounting detecting step of confirming whether the displacement pre-correction reference mark positions are respectively contained in predetermined reference mark searching ranges;

a processing stopping step of stopping processing when the displacement pre-correction reference mark positions are all disposed outside the predetermined reference mark searching ranges in the incorrect mounting detecting step; and a sensor displacement correcting step of performing linear coordinate transformation on the gray image such that the displacement pre-correction reference mark positions are aligned with respective displacement post-correction reference mark positions when the displacement pre-correction reference mark positions are contained in the respective predetermined reference mark searching ranges in the incorrect mounting detecting step.

16. The liquid sample analyzing method according to claim 13, wherein in the reference mark detecting step, the gray image is binarized by a predetermined threshold value and the displacement pre-correction reference mark position of the at least one reference mark is a barycenter of a connected component.

* * * * *